United States Patent [19]

Anazawa et al.

[11] Patent Number: 5,833,827
[45] Date of Patent: Nov. 10, 1998

[54] CAPILLARY ARRAY ELECTROPHORESIS SYSTEM

[75] Inventors: Takashi Anazawa, Kokubunji; Satoshi Takahashi, Kunitachi; Hideki Kambara, Hachioji, all of Japan

[73] Assignee: Hitachi, Ltd., Tokyo, Japan

[21] Appl. No.: 710,894

[22] Filed: Sep. 23, 1996

[30] Foreign Application Priority Data

Sep. 29, 1995 [JP] Japan ................................. 7-252401
Nov. 30, 1995 [JP] Japan ................................. 7-311951

[51] Int. Cl.$^6$ ........................ G01N 27/26; G01N 17/447
[52] U.S. Cl. ........................................ 204/603; 204/452
[58] Field of Search ................................ 504/451, 452, 504/453, 454, 455, 601, 602, 603, 604, 605

[56] References Cited

U.S. PATENT DOCUMENTS 5,312,535  5/1994  Waska et al. ........................... 204/603
5,582,705  12/1996  Yeung et al. ........................... 204/603

FOREIGN PATENT DOCUMENTS 6-138037  5/1994  Japan .

OTHER PUBLICATIONS

Analytical Chemistry, 1990, May vol. 62, "High–Speed Separations of DNA Sequencing Reactions by Capillary Electrophoresis", H. Drossman et al, pp. 900–903.
Nature, vol. 359, Sep. 10, 1992, "Capillary array electrophoresis: an approach to high–speed, high–throughput DNA sequencing", Mathies et al, pp. 167–169.
Nature, vol. 361, Feb. 11, 1993, "Multiple–sheathflow capillary array DNA analyzer", H. Kambara et al, pp. 565–566.

Analytical Chemistry, vol. 65, No. 7, Apr. 1, 1993, "Multiplexed Fluorescence Detector for Capillary Electrophoresis Using Axial Optical Fiber Illumination", J. Taylor et al, pp. 956–960.
Analytical Chemistry, May 1994, vol. 66, Simultaneous Monitoring of DNA Fragments SEpaated by Elctrophoresis in a Multiplexed Array of 100 Capillaries, K. Ueno et al, pp. 1424–1431.
Applied Spectroscopy, vol. 49, No. 5, 1995, "Optimization of Excitation and Detection Geometry for Multiplexed Capillary Array Electrophoresis of DNA Fragments", Xiandan Lu et al, pp. 605–609.
Electrophoresis, No month available 1992, vol. 13, "Formamide modified polyacrylamide gels for DNA sequencing by capillary gel electrophoresis", M. Rocheleau et al, pp. 484–486.

Primary Examiner—Robert J. Warden
Assistant Examiner—John S. Starsiak, Jr.
Attorney, Agent, or Firm—Fay, Sharpe, BEall, Fagan, Minnich & McKee

[57] ABSTRACT

The capillary array electrophoresis system of the present invention comprises a plurality of capillaries whose inside is filled with migration medium and at least parts of which are aligned in a plane, a means for making lasers substantially simultaneously irradiate transparent parts of the plurality of capillaries along the direction of alignment of the plurality of capillaries so as to excite fluorephore labels of migrated and separated samples, a fluorescence detection means for detecting fluorescence radiating from the fluorephore labels, from a direction crossing the direction of the alignment, the transparent parts of the plurality of capillaries are surrounded by a transparent gas, the cross section of the capillary of the transparent part is a circle and the ratio of the outside diameter to the inside diameter of the capillary ranges from 1 to 7.

11 Claims, 15 Drawing Sheets

FLUORESCENCE DETECTION

FLUORESCENCE DETECTION

FLUORESCENCE DETECTION

CAPILLARY ARRAY ELECTROPHORESIS SYSTEM

BACKGROUND OF THE INVENTION

The present invention relates to a separation analysis system for DNA, RNA or proteins, etc., and more particularly to the sequencing of DNA and RNA, and to a capillary array electrophoresis system effective for detection of polymorphism of restriction endonuclease fragments based on the variety of individual base sequences.

The techniques for analyzing DNA or RNA, etc. have become increasingly important in the fields of medicine and biology including genetic analysis and genetic diagnosis. Particularly, the development of a high speed, high-throughput DNA analyzer has proceeded recently in connection with a genome analysis initiative. In a DNA analysis, a fluorophore labeled sample is separated by molecular weight by gel electrophoresis, a laser irradiates the sample to detect the fluorescence radiated from the fluorophore label, and the serial signals obtained are analyzed. In a gel electrophoresis, a slab gel is widely used in which acrylamide is polymerized between two glass plates with interstice of approximately 0.3 mm (slab gel electrophoresis). The sample injected from an end (upper end) is migrated toward the other end (lower end), separated by molecular weight by an electric field applied at the both ends of the slab gel. A laser is irradiated on a position with a constant distance from the starting point of migration to all the migration paths at a time from the side of the slab gel. The detection of fluorescence with the laser irradiation is performed periodically in series with a constant time interval. The DNA sequencing is performed by analyzing the detection results.

Recently, instead of a slab gel, a capillary gel in which gel is polymerized in fused silica capillaries has been used. Capillary gel electrophoresis, allowing to apply an electric field higher than that applied to the slab gel electrophoresis above, has come into notice as a method capable of high speed and high resolution (Analytical Chemistry 62, 900 (1990)). In a common capillary gel electrophoresis, an on-column detection is performed in which using one capillary, a laser directly irradiates onto the capillary in the proximity of the lower end and the fluorescence radiated from the fluorophore labeled sample migrating in the capillary is detected. Since all the outer surface of a capillary is treated with polyimide coating, the coating at the position for detecting fluorescence is removed to leave a window with exposed glass (U.S. Pat. No. 5,312,535 (May 17, 1994)). By the laser irradiated at the position where glass is exposed, the separated component of the fluorophore labeled sample migrating inside the capillary with electrophoresis is excited and radiates fluorescence. The fluorescence is detected periodically in series with a constant time interval, and analyzed for DNA sequencing.

However, the on-column detection system above does not have high-throughput in spite of its high speed analysis, because a high scattering on the capillary surface allows the use of only one capillary at a time. Recently, several examples of a high-throughput capillary array gel electrophoresis system with a plurality of capillaries arranged to analyze many samples at a time in high speed have been reported.

The first example is a capillary array scanning method (Nature, 359, 167(1992)), in which a laser orderly irradiates a plurality of capillaries one by one to perform on-column fluorescence detection. This system adopts a confocal geometry in which the position where a laser beam is most focused in the capillary and the position of the source of light coming into a fluorescence detector (fluorescent light-intercepting optical system) concur that allows independent detection of an individual capillary. The laser irradiation and the fluorescent light-intercepting optical system are fixed while a stage holding the capillary array is moved in a one-dimensional direction to make a laser irradiate each capillary in a sequential order.

The second example is a capillary array sheath-flow method (Nature, 361, 565–566 (1993), Japanese Patent Application Laid-Open No. 6-138037). This system performs off-column detection, in which the lower end of a capillary array is immersed into a buffer solution, the sample component separated by molecular weight by gel electrophoresis is eluted as it is into the buffer solution, and the fluorescence radiated from the sample component is detected in a capillary-free spatial part (in the specification of this application, the method in which the fluorescence radiated from the sample component is detected in a capillary-free spatial part is called off-column detection for simplicity in contrast with on-column detection in which the fluorescence radiated by laser irradiation onto a capillary from a fluorophore labeled sample is detected).

Moreover, by allowing the buffer solution to slowly flow in the direction of sample migration, the cross talk of separated components eluted from different capillary gels in the buffer solution or the cross talk of two components separated in one capillary gel in the buffer solution is prevented. By making a laser irradiate the spatial part where no capillary is present but the buffer solution is present in the proximity of a capillary array outlet to avoid the problem of a laser beam scattering on the capillary surface, components eluted from a plurality of capillaries are substantially excited in a batch and fluorescence detection is performed substantially at the same time.

The third example irradiates the laser from a single light source split by a beam splitter, etc. onto each of a plurality of capillaries for simultaneous on-column detection of a plurality of capillaries without mechanical scanning of a plurality of capillaries (Analytical Chemistry 65, 956 (1993)).

The fourth example irradiates a laser light spread by a cylindrical lens in the direction of capillary array onto a plurality of capillaries in a batch (Analytical Chemistry 66, 1424 (1994)).

The fifth example simultaneously irradiates a plurality of capillaries by allowing a laser to come from the side of the capillary array plane, with the detecting part of a plurality of capillaries arranged on a plane and the outside of the capillaries in a part filled with water (Appl. Spectrosc. 49 (1995) 605). The outside of the capillaries is filled with water and the difference in refractive indices between the outside of the capillaries and the capillaries themselves is small, so as to suppress the reflection of a laser on the capillary surface.

SUMMARY OF THE INVENTION

Because the capillary array scanning method of the first example above performs fluorescence detection of capillaries one by one in a sequential order, it has less time allowed for fluorescence detection of one capillary than a common on-column detection using one capillary. In cases where an array of n capillaries are used, the time allowed for fluorescence detection of one capillary is 1/n at the longest compared with a common on-column detection, and it is practically 1/n or shorter because the glass part of a capillary, through which no separated component of a sample passes, is detected. Consequently, the problem that fluorescence detection sensitivity decreases arises. In other words, a time that is n times longer than the fluorescence detection time in a common on-column detection, or even a longer time, is needed to obtain a detection sensitivity similar to that of the common on column detection using one capillary.

The time interval of adjacent peaks in electrophoresis migration patterns of components separated in one capillary becomes shorter in higher speed analysis. A time necessary for one time scanning of an array of n capillaries considerably larger than the time interval of adjacent peaks causes a problem that the resolution of the electrophoresis pattern of separated components decreases. Furthermore, the system of the first example has a structure which leads to a lot of failure with a movable stage part for performing mechanical scanning.

The capillary array sheath-flow method of the second example has a problem that the fluorescence intensity obtained from the component separated by molecular weight becomes lower as the molecular weight increases compared with that of on-column detection. The problem is caused by the following reasons. It is necessary to steadily flow a buffer solution with a constant speed or higher so that the separated components eluted from the lower end of a capillary gel into the buffer solution do not mix with each other in the buffer solution by diffusion, etc. On the other hand, the migration speed of the sample components that migrate and are separated by molecular weight becomes lower as the molecular weight is larger. As the migration speed of the sample component in the capillary gel compared with the flow speed of the buffer solution is lower, the sample component is largely expanded in the direction of migration when the sample component is eluted from the capillary gel into the buffer solution.

The third and fourth examples above have a problem that they cannot detect the sample components separated by migration with good sensitivity because the intensity of the laser light irradiated onto each column is reduced.

The fifth example above has a problem that it has a decreased number of capillaries which can be irradiated substantially at the same time because, the more capillaries are arranged along the laser irradiation axis, the lower the intensity of the irradiating laser light.

It is an object of the present invention to provide a capillary array electrophoresis system which can make a laser irradiate a plurality of capillaries substantially at the same time and detect fluorescence radiated from fluorophore labeled sample components migrating in a plurality of capillaries substantially at the same time in a batch, performing on-column fluorescence detection, without mechanical scanning of a plurality of capillaries, or without optical scanning of a laser beam, so as to solve the problems of the prior art described above.

The capillary array electrophoresis system of the present invention is a multiple focusing capillary array electrophoresis system which has a plurality of capillaries arranged on the same plane, and a laser irradiates from a direction parallel to the plane to simultaneously irradiate a plurality of capillaries for on-column detection. More specifically, the capillary array electrophoresis system of the present invention is characterized as follows:

(1) In an electrophoresis system in which a laser irradiates a plurality of capillaries to detect fluorescence, on-column detection is performed in which a laser irradiates a position of the capillaries filled with electrophoretic separation medium, at least the positions of the capillaries which a laser irradiates (the transparent part of a capillary where a laser irradiates has a circular section and the outside of the transparent part of the capillary is a transparent gas) are made of a transparent material, at least the positions of the capillaries which a laser irradiates are arranged in a plane feature, and a laser irradiates in parallel the array plane from a lateral of the array of capillaries so as to perform simultaneous irradiation of a plurality of capillaries. The ratio of outside diameter to inside diameter of a capillary at the position where a laser shall irradiate ranges from 1 to 7 or from 3 to 5. The capillary array pitch at the transparent part shall not be more than four times as large as the outside diameter of the capillary. The outside of the transparent part of a capillary which is a transparent gas may be substituted with a transparent liquid, in which case the ratio of outside diameter to inside diameter of a capillary at the transparent position shall be less than 2 and the capillary array pitch at the transparent part shall not be more than four times as large as the outside diameter of the capillary.

(2) In an electrophoresis system in which a laser irradiates a plurality of capillaries to detect fluorescence, on-column detection is performed in which a laser irradiates a position of the capillaries filled with electrophoretic separation medium, at least the positions of the capillaries which a laser irradiates (the transparent part of a capillary where a laser irradiates has an elliptic section) are made of a transparent material, at least the positions of the capillaries which a laser irradiates are arranged in a plane feature, and a laser irradiates in parallel the array plane from a side of the array of capillaries so as to perform simultaneous irradiation of a plurality of capillaries. A plurality of capillaries are arranged in a plane feature with the semi-minor axis of the ellipse parallel to the capillary array plane and the semi-major axis perpendicular to the capillary array plane, or with the semi-major axis of the ellipse parallel to the capillary array plane and the semi-minor axis perpendicular to the capillary array plane. The outer side of the capillary at the transparent part shall be a transparent gas or a transparent liquid.

(3) In an electrophoresis system in which a laser irradiates a plurality of capillaries to detect fluorescence, on-column detection is performed in which a laser irradiates a position of the capillaries filled with electrophoretic separation medium, at least the positions of the capillaries which a laser irradiates (the section of the transparent part of a capillary where a laser irradiates is square or rectangular, and the transparent part of the capillary has two sets of nearly parallel planes) are made of a transparent material, at least the positions of the capillaries which a laser irradiates are arranged in a plane feature (so that one edge of the sectional feature will be parallel to the capillary array plane), and a laser irradiates in parallel the array plane from a side of the array of capillaries so as to perform simultaneous irradiation of a plurality of capillaries. The outside of the capillary shall be either a transparent gas, a transparent liquid or a transparent solid. In cases of a transparent solid, the outside is preferably made of glass, particularly fused silica.

Furthermore, in the electrophoresis systems of (1) to (3), acrylamide gel or its derivative, or a polymer is filled in the capillary as a migration medium. In the electrophoresis systems above, at least two kinds of capillaries with different sectional features may also be connected in between a sample injection end and the position to detect fluorescence. Also in the electrophoresis systems above, a single layer vapor deposition antireflection coating is applied on at least the surface of the part where fluorescence is detected.

For the laser irradiation in the system described above, all of a plurality of capillaries may be irradiated, and the transmitted light may be reflected by a total reflection mirror and the plurality of capillaries irradiated again along the reverse path, or a laser beam split into two using a beam splitter may be irradiated from two directions, the sides of a capillary array as opposed to each other, and the transmittance of a laser wavelength of a fluorescence detection filter is preferably $10^{-5}$ or less.

Furthermore, the capillary array electrophoresis system of the present invention is characterized in that, the inside is filled with migration medium, and at least part of the array is arranged in a plane feature. The system has a means to make a laser irradiate a transparent part of the plurality of capillaries substantially at the same time along the direction of the array for exciting the fluorophore label of a sample migrated and separated, and a fluorescence detection means to detect the fluorescence radiated from the fluorophore label from a direction crossing the above direction of the array, following an equation;

$$(360/\pi)[-\sin^{-1}\{r/(2R)\}+\sin^{-1}\{rn_1/(2Rn_2)\}-\sin^{-1}\{n_1/(2n_2)\}+\sin^{-1}\{n_1/(2n_3)\}]\leq 4°, \quad (4)$$

or $$(360/\pi)[-\sin^{-1}\{r/(2R)\}+\sin^{-1}\{rn_1/(2Rn_2)\}-\sin^{-1}\{n_1/(2n_2)\}+\sin^{-1}\{n_1/(2n_3)\}]\leq 1°, \quad (5)$$

wherein $2R$, $2r$ and $n_2$ are respectively an outside diameter, an inside diameter and a refractive index of each capillary above which the laser above transmits, $n_1$ is a refractive index of the medium outside of each capillary above and $n_3$ is a refractive index of the medium inside of each capillary above.

According to the present invention, conducting on-column detection of fluorescence without performing laser beam scanning, a plurality of capillaries can be irradiated by a laser substantially at the same time in a single batch, accomplishing a highly sensitive, high-speed and high-throughput analysis. Yet the system construction and capillary array are quite simple and practical. The use of replaceable migration medium including polymers, etc. allows repetitive utilization without moving the capillary array itself, cutting a great deal of costs and labor.

The present invention is summarized as follows: A plurality of capillaries are arranged on a glass plane and a laser irradiates from a side of the array along the array axis. The capillaries acquire a convex lens function by means of the relations between the outside diameter and the inside diameter of the capillaries, the refractive index of the medium outside of the capillaries, the refractive index of the capillaries and the refractive index of the medium inside of the capillaries. The laser beam is repeatedly focused and proceeds in the capillary array without deviating from the capillary array axis. Consequently, sufficient laser power reaches the inside of each capillary, which allows simultaneous fluorescence detection, realizing a high sensitivity, high speed and high throughput.

DESCRIPTION OF THE PREFERRED EMBODIMENTS

Figure 1A:
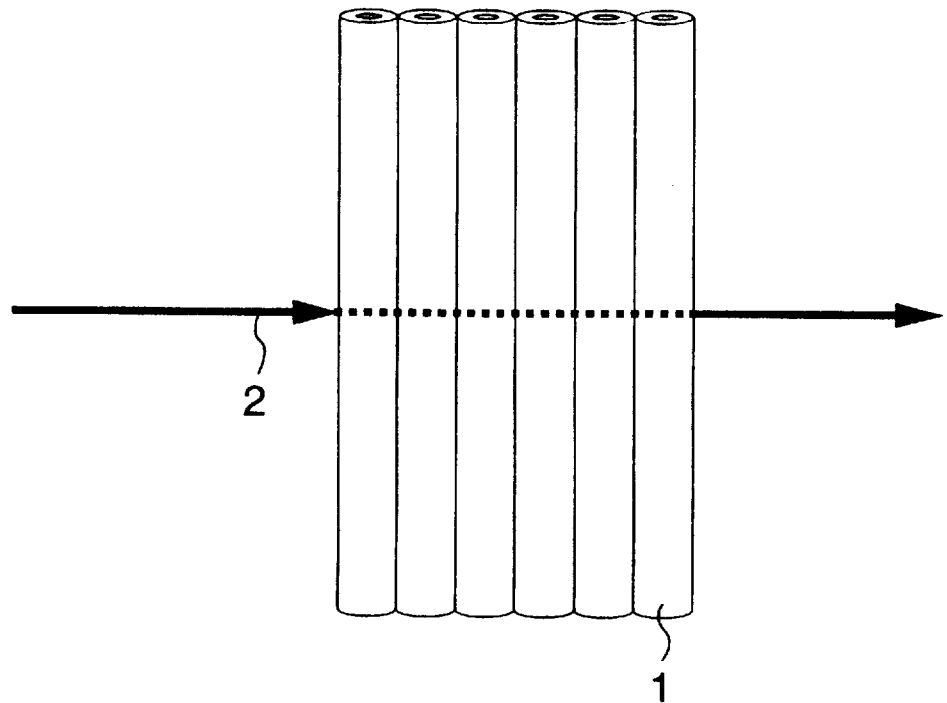
FIG. 1A is a plan view illustrating the construction of the major part of the capillary array electrophoresis system which performs on-column detection of the capillary array of the present invention.
Figure 1B:
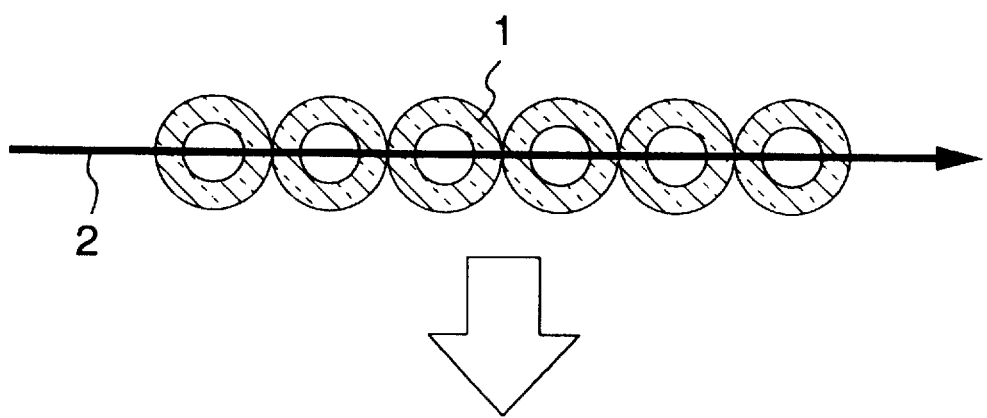
FIG. 1B is a cross-sectional view illustration the construction of the major mart of the capillary array electrophoresis system which performs on-column detection of the capillary array of the present invention.

FIG. 1 illustrates the major part of a multi-focus capillary array electrophoresis system in which a plurality of capillaries 1 (an example of six capillaries is shown in FIG. 1) are arranged in the same plane, and a laser 2 is irradiated from a direction nearly perpendicular to the migration direction of a sample to excite the fluorophore labeled sample components migrating in a plurality of capillaries substantially at the same time for detecting the sample components by on-column detection. FIG. 1A is a view seen from the plane direction of the array of a plurality of capillaries, and FIG. 1B is the cross section view. A plurality of capillaries which a laser 2 irradiates are either separation capillaries or the detection capillaries for detecting separated sample components that are connected with each of a plurality of separation capillaries. Laser 2 is irradiated to a site with a particular distance from the starting point of migration of the sample on a capillary filled with gel (separation capillary), or to a particular site of a detection capillary filled with gel.

In the multiple focusing capillary array electrophoresis system of the present invention, a sample which is subjected to migration separation analysis contains a plurality of fluorophore labeled components. If a component itself contained in a sample radiates fluorescence by laser irradiation, no fluorophore labeling is necessary. Also in respective figures including FIG. 1 referred to below, respective means such as a power source for applying an electric field for migrating a sample, and an electrode bath for housing electrodes and an electrolyte, as well as a processor unit for processing detection signals after detecting fluorescence from a sample migrating in capillaries 1, an indicator indicating the processing result, a control unit controlling respective parts of the multiple focusing capillary array electrophoresis system, and a laser source are omitted. In the descriptions below, on the assumption that a laser 2 finely focused is injected toward the direction of a line connecting the central axis of each capillary of a plurality of detection capillaries or a plurality of separation capillaries, and the laser 2 ideally proceeds straight without being refracted or scattered, the straight line interconnecting the central axes of each capillary within a plane perpendicular to the central axes of each capillary and including a laser 2 is called a capillary array axis.

EXAMPLE 1

In this example, cylindrical capillaries with a circular section are used. The multiple focusing capillary array electrophoresis system of the present invention has two features: (1) It allows laser power to reach many capillaries, and (2) it reduces the background light by scattering of a laser beam. The conditions to realize (1) were revealed by the calculation demonstration described below.

Figure 2:
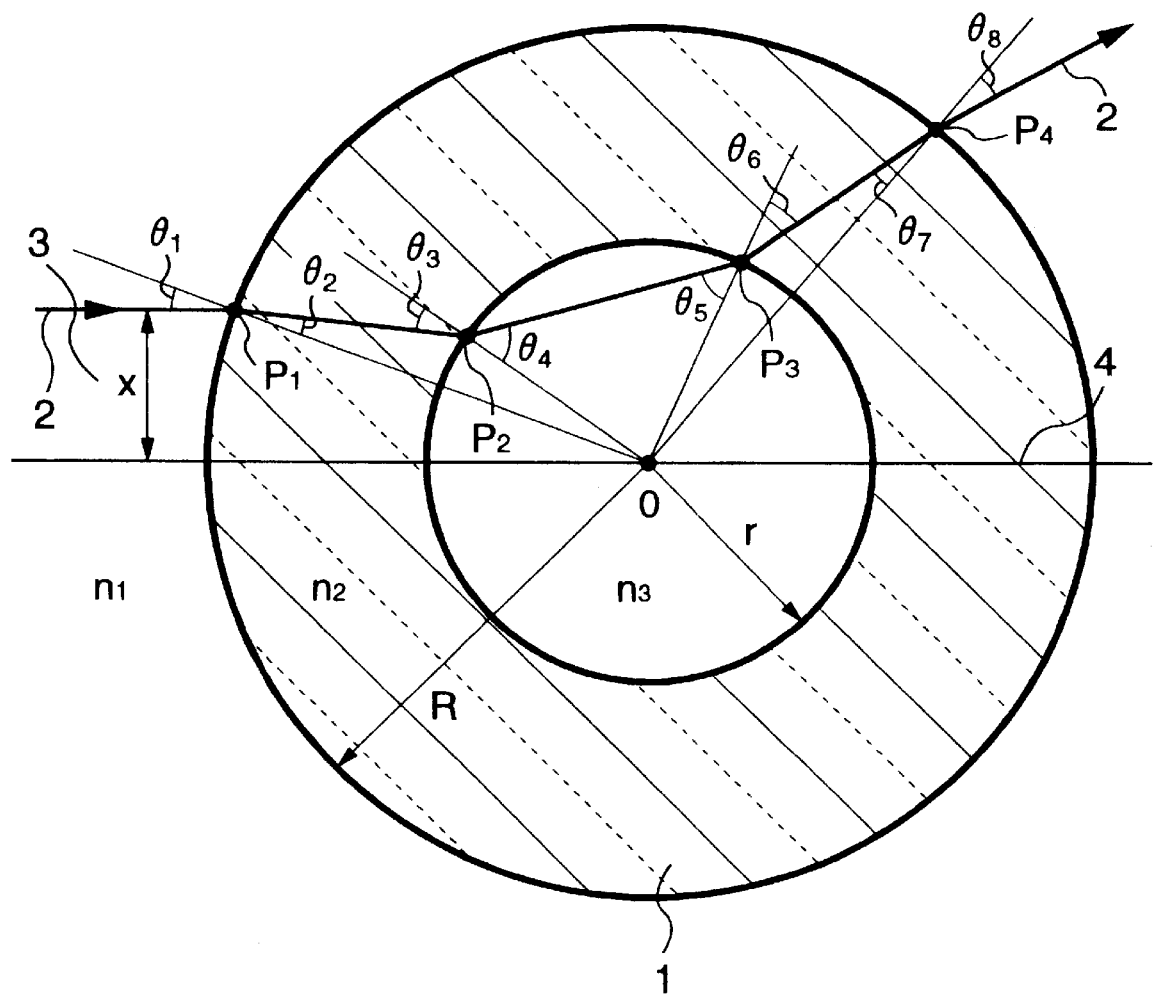
FIG. 2 is a cross-sectional view illustrating the optical path of a laser beam in the capillary of the present invention.

FIG. 2 is a cross-sectional view of a cylindrical capillary with outside diameter 2R and inside diameter 2r. It shows the manner of an optical path of a laser beam 2 with an infinitesimal width which came into a position with a distance x from a capillary array axis 4, the optical path changed by refraction with the capillary 1. The laser beam passes boundaries where the refractive index changes four times (or twice) with each capillary. That is, the laser beam 2 is refracted at the four points of P1 which is a position where the laser comes from the outside of the capillary 1 into the capillary 1, P2 which is a position where the laser comes from the capillary 1 into the inside of the capillary 1, P3 which is a position where the laser goes from the inside of the capillary 1 out into the capillary 1, and P4 which is a position where the laser goes from the capillary 1 out into the outside of the capillary 1.

However, P2 or P3 sometimes may not exist because the laser beam 2 may not pass the inside of the capillary according to the path of the laser beam 2. The incidence angle and refraction angle at $P_1$, $P_2$, $P_3$ and $P_4$ are $\theta_1$, $\theta_2$, $\theta_3$, $\theta_4$, $\theta_5$, $\theta_6$, $\theta_7$, $\theta_8$, respectively. The refractive index of the medium outside of the capillary is represented by $n_1$, the refractive index of the material of the capillary is represented by $n_2$, and the refractive index of the medium capillary is represented by $n_3$.

The use of the geometrical relation shown in FIG. 2 and Snell's law on the respective boundary faces derive (Equation 1) to (Equation 8).

$\theta_1 = \sin^{-1} \{x/R\}$ (Equation 1)

$\theta_2 = \sin^{-1} \{(n_1/n_2) \sin \theta_1\}$ (Equation 2)

$\theta_3 = \sin^{-1} \{(R/r) \sin \theta_2\}$ (Equation 3)

$\theta_4 = \sin^{-1} \{(n_2/n_3) \sin \theta_3\}$ (Equation 4)

$\theta_5 = \theta_4$ (Equation 5)

$\theta_6 = \theta_3$ (Equation 6)

$\theta_7 = \theta_2$ (Equation 7)

$\theta_8 = \theta_1$ (Equation 8)

The angle between the laser beam before coming into a capillary and the laser beam after transmission is represented by the angle of refraction $\Delta\theta$. $\Delta\theta$ is represented by (Equation 9) according to FIG. 2.

$$\begin{aligned} \Delta\theta &= -(\theta_1 - \theta_2) - (\theta_3 - \theta_4) + (\theta_5 - \theta_6) + (\theta_7 - \theta_8) \quad \text{(Equation 9)} \\ &= 2(-\theta_1 + \theta_2 - \theta_3 + \theta_4) \\ &= 2\{-\sin^{-1}(x/R) + \sin^{-1}(xn_1/(Rn_2)) - \\ &\quad \sin^{-1}(xn_1/(rn_2)) + \sin^{-1}(xn_1/(rn_3))\} \end{aligned}$$

$\Delta\theta$ differs with the incidence position x of the laser beam, and can be controlled by the outside diameter of the capillary R, the inside diameter r, the refractive index of the outside of the capillary $n_1$, the refractive index of the material of the capillary $n_2$ and the refractive index of the inside of the capillary $n_3$. The laser beam with x=0 always gives $\Delta\theta=0$, and with the increase of x, $|\Delta\theta|$ also simply increases (x≦r is assumed here). Thus, the capillary itself has an action of a lens with unfixed focus, which is a concave lens when $\Delta\theta>0$, or a convex lens when $\Delta\theta<0$. When $n_1=n_2=n_3$, $\Delta\theta=0$ for any x, of course.

In the case where a laser beam irradiates the array formed by aligning a plurality of capillaries in a plane feature from a side of the array so that the laser beam will pass a plurality of the capillaries, it is more advantageous for making the laser power reach a plurality of the capillaries when the angle of refraction by the capillary $\Delta\theta$ is smaller; particularly, respective capillaries have more convex lens action for $\Delta\theta<0$. For each capillary, focusing a transmitting laser beam more than an incident laser beam allows the laser power to reach efficiently to the next capillary. For $n_2>n_3$ under normal conditions, $\Delta\theta$ becomes smaller as n1 becomes smaller based on Equation 9. Thus, it is a preferable condition to fill the outside of the capillary with a transparent gas with $n_1=1.00$ such as air.

On the other hand, the laser beam is also reflected at each boundary. That is, a part of the laser power of the incident light becomes reflected light and the remainder becomes refracted light (transmitted light). When the ratio of the laser power of the reflected light to the laser power of the incident light is represented by a reflectance $R_{ef}$, and the ratio of the laser power of the refracted light to the laser power of the incident light is represented by a transmittance $T_{ra}$, these are functions of the incident angle $\theta_i$ and the angle of refraction $\theta_t$ (i.e. the refractive indices of both media) represented by Equations 10 and 11.

$$2R_{ef}=\tan^2(\theta_i-\theta_t)/\tan^2(\theta_i+\theta_t) +\sin^2(\theta_i-\theta_t)/\sin^2(\theta_i+\theta_t) \quad \text{(Equation 10)}$$

$$2T_{ra}=\sin(2\theta_i)\sin(2\theta_t)\{1/\cos_2(\theta_i-\theta_t)+1\}/\sin^2(\theta_i+\theta_t) \quad \text{(Equation 11)}$$

Wherein $R_{ef}+T_{ra}=1$. The case shown here has no polarization in the incident light. The laser power decreases orderly every time it passes a boundary in accordance with Equations 10 and 11. Therefore, by multiplying the optical path in the capillary in which sample components pass (the length connecting the point $P_2$ with the point $P_3$ in FIG. 2) by the laser power at the position, the excitation efficiency of the laser beam in the capillary (the excitation efficiency of sample components migrating in the capillary by the laser beam) was estimated. Also, representing the position where a laser beam with an infinitesimal width by the distance x from the capillary array axis (x=0), the excitation efficiency of a laser beam with a finite width was estimated by changing the distance x. Furthermore, how the excitation efficiency in each of a plurality of capillaries changes in cases where a plurality of capillaries are arranged in a plane feature was investigated by serial calculations above.

As an example, a 50-cm-long fused silica capillary of circular section having an outside diameter of 0.375 mm (R=0.1875 mm) and a inside diameter of 0.1 mm (r=0.05 mm). An acrylamide solution of concentration 4% T (total monomer concentration) and 5% C (crosslinking material concentration) containing 7M urea as a denaturing agent was injected, and then allowed to gel (n3=1.36). A window to detect fluorescence had been preliminarily formed as a laser irradiation site by removing the polyimide coating over 10 mm of length all around each capillary at a position 30 cm from the sample injection end of the capillary.

Figure 3:
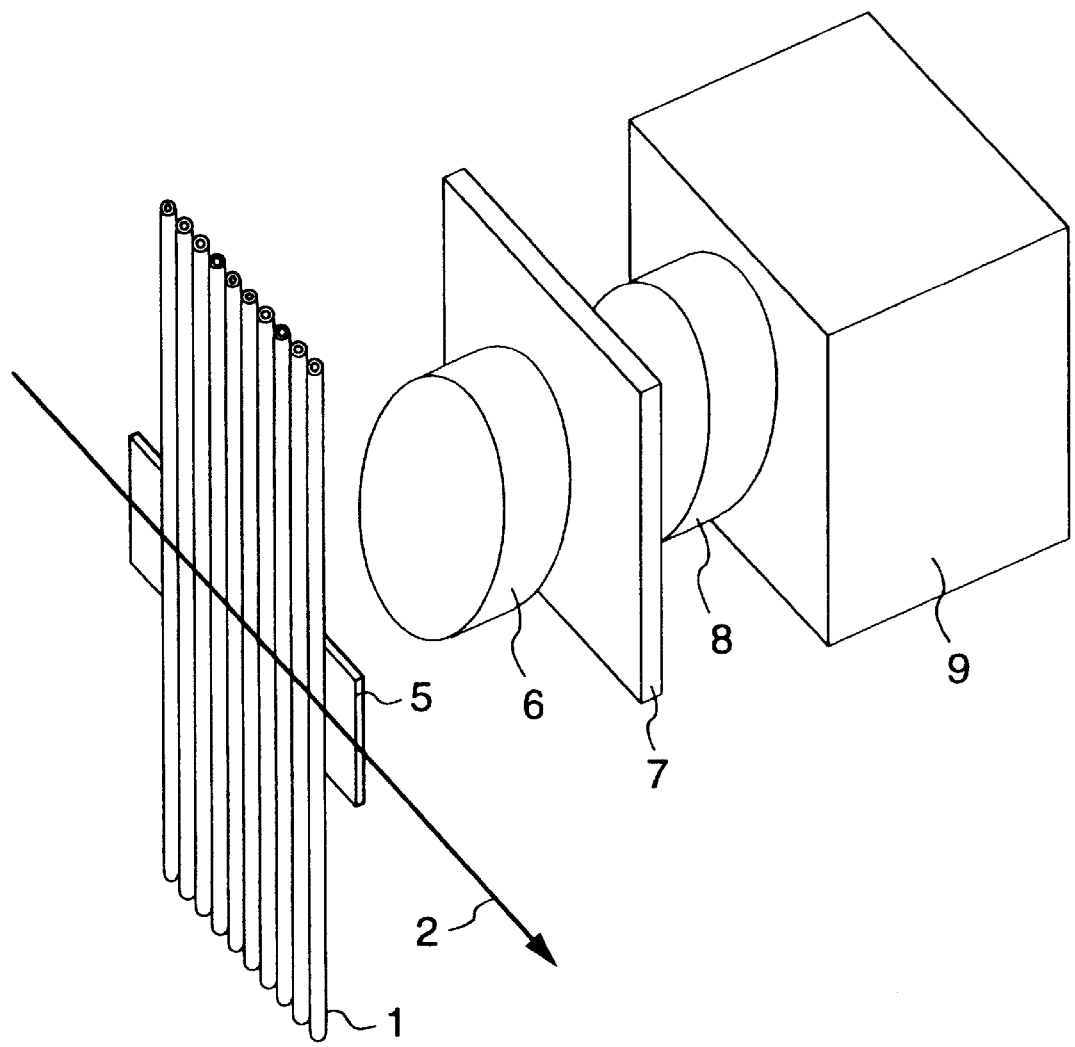
FIG. 3 is a diagram illustrating the system construction of Example 1 of the present invention.

As shown in FIG. 3, the detection parts of capillary gels were made all of uniform pitch of 0.375 mm, and respective capillaries were arranged in a plane feature in a close-pack configuration fixed on a glass plate 5. Air ($n_1$=1.00) was provided outside of the capillary at the fluorescence detection. The fluorescence detection was performed with a 2D detector 9 from the direction perpendicular to the capillary array plane via the first lens 6, a bandpass filter 7 and the second lens 8. It was necessary to reduce the transmittance of the laser wavelength more than that of the bandpass filter used at the time of detecting fluorescence in a slab gel electrophoresis, etc. because the reflection of the laser beam 2 by the capillary was large in these experimental conditions. Therefore a bandpass filter with $10^{-5}$ or less of the transmittance of the laser wavelength was used.

Figure 4:
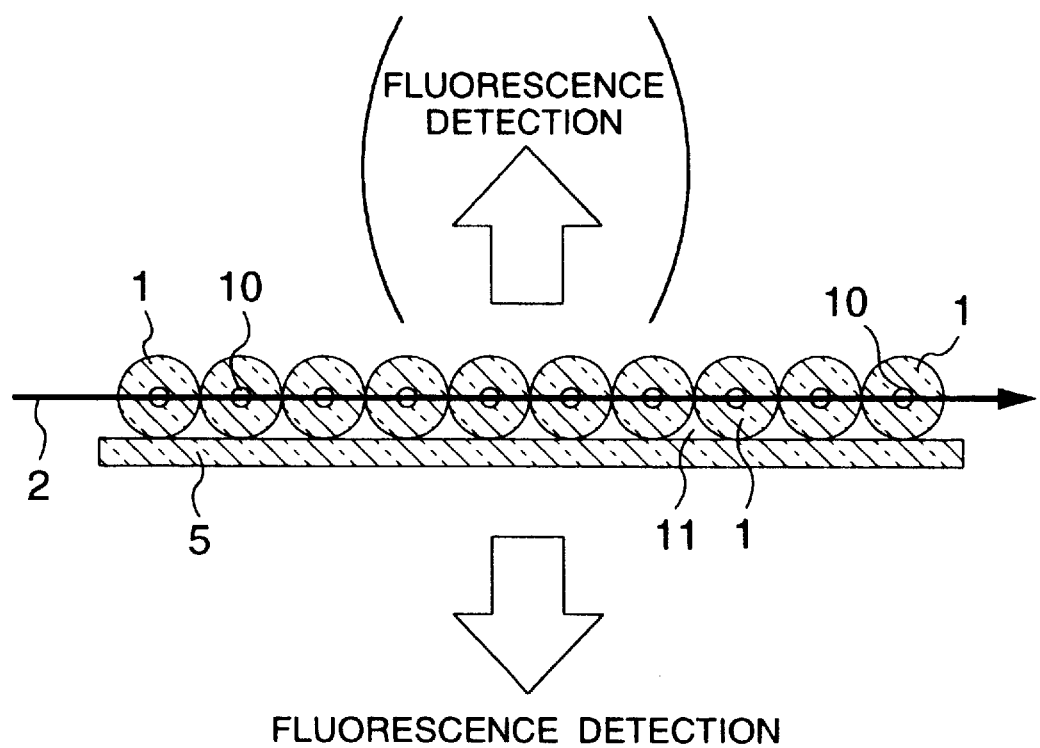
FIG. 4 is a cross-sectional view of the part where fluorescence is detected in Example 1 of the present invention.
Figure 5:
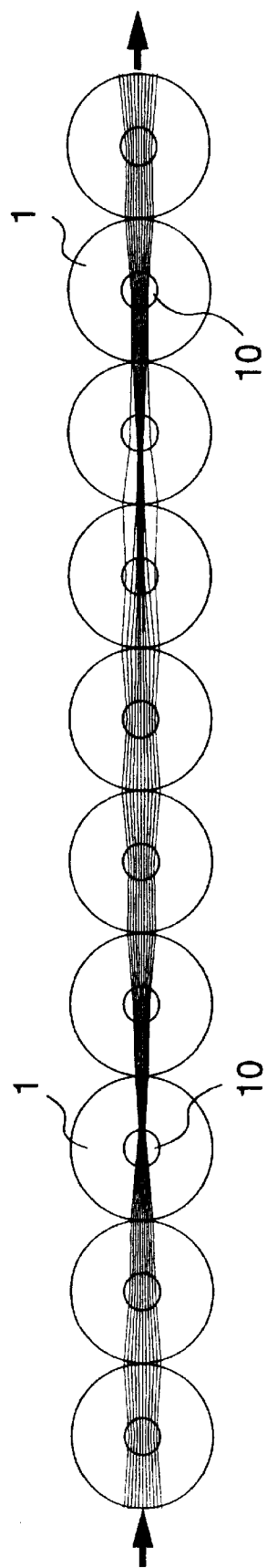
FIG. 5 is a diagram illustrating the simulation result of the optical path in the capillary array in Example 1 of the present invention.

FIG. 4 shows a cross-section view cutting the capillary axes at the fluorescence detection sites. A laser was converged to a beam diameter of 0.1 mm and made to go into the capillary array from the side through the capillary array axis. At this time, $\Delta\theta<0$ for any laser beam of $x \leq r$ from Equation 9, and each capillary had an action of a convex lens. From the inside diameter and outside diameter of the capillary above and the refractive index of the medium, $\Delta\theta=-1.76°$ based on Equation 18 below, and both Equations 20 and 22 were satisfied. The beam width of 0.1 mm was thought to be divided into 11 infinitesimal beam components. The beam components come into the first capillary at the positions with distances x from the capillary array axis (laser beam central axis, x=0) are 0.00, ±0.01, ±0.02, ±0.03, ±0.04, ±0.05 mm. FIG. 5 shows the result of the simulation of the optical path drawn by the transmitted light of each beam component while proceeding through the capillary array. FIG. 5 shows a cross-section view cutting the capillary axes of the fluorescence detection sites. That is, a laser beam goes into the left capillary and comes out from the right capillary.

All calculations of the optical paths were performed in series on the assumption that 10 capillaries are arranged as above. The beam component (x=0.00) which locates the central axis of the laser beam proceeds rectilinearly on the capillary array axis because it is not refracted at all and $\Delta\theta=0$, as its incident angle at any boundary is 0°. The beam components other than the one with x=0.00 are refracted basically to a direction toward the capillary array axis by the convex lens action of the capillary, and they proceeded along optical paths in the capillary array fluttering up and down, centering at the capillary array axis. The amplitude and frequency varied with different beam components, but the optical path of each beam component was symmetrical with respect to the capillary array axis. It was revealed from all above that all the beam components transmit the inside of all the 10 capillaries without deviating to the outside, and contribute to excitation of the sample components migrating in the capillaries. In other words, the capillary electrophoresis system of the present invention may be appropriately called a multiple focusing capillary electrophoresis system, because the laser beam irradiating each capillary gel forms an optical path of approximate focus in each of a plurality of capillary gels.

Figure 6:
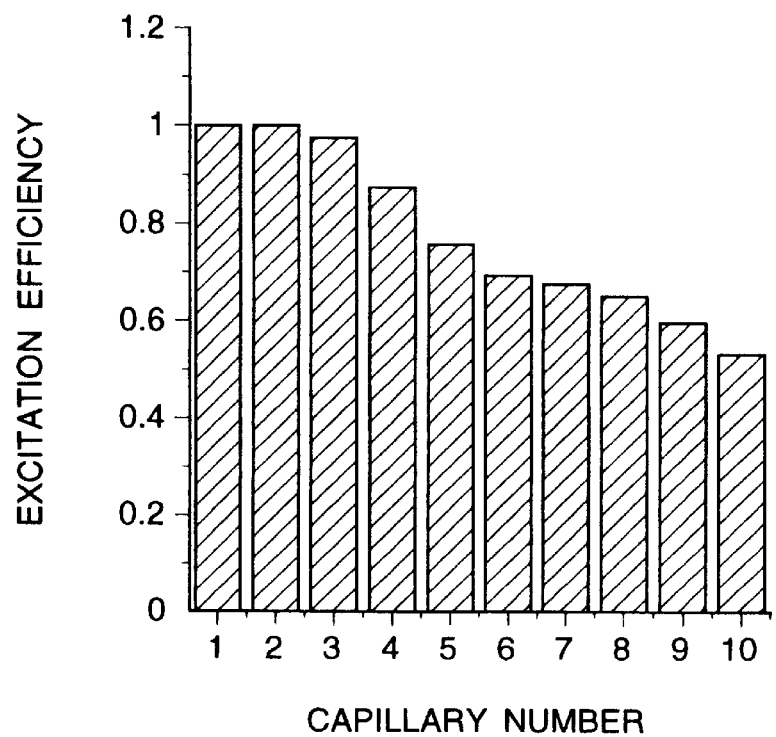
FIG. 6 is a graph showing the relation between the position of the capillaries and excitation efficiency in Example 1 of the present invention.

The length of the optical path transmitting the inside of a capillary (optical path length) was calculated with each capillary, the optical path length was multiplied with the laser Dower at the position, the products were accumulated for all of the beam components, and the accumulated value was made to represent the excitation efficiency in each capillary, so as to evaluate the degree of the decrease of the excitation efficiency in each capillary. FIG. 6 shows the excitation efficiency in each capillary calculated as above (the excitation efficiency in each capillary is normalized by the excitation efficiency in the first capillary on the laser source side). In FIG. 6, each capillary is numbered 1 to 10 in order from the laser source side.

Since the laser power of all of the beam components was reduced by reflection at every pass of a boundary where a refractive index changes, the excitation efficiency with every capillary exponentially decreased as shown in FIG. 6. The fluorescence from each capillary actually detected was proportional to the excitation efficiency. As shown in FIG. 6, the excitation efficiency of the tenth capillary was as high as 54.1% of the first capillary. Calculation of the mean transmittance of the laser beam per capillary from this value resulted in a high efficiency of 93.4% ($0.934^9 \approx 0.541$). Assuming that the decrease of the excitation efficiency which allows simultaneous detection is up to 20% from the relation between the sensitivity and the dynamic range of the detector, simultaneous detection of up to 24 capillaries was possible on these calculation demonstration conditions ($0.934^{23} \approx 0.21$).

Figure 7:
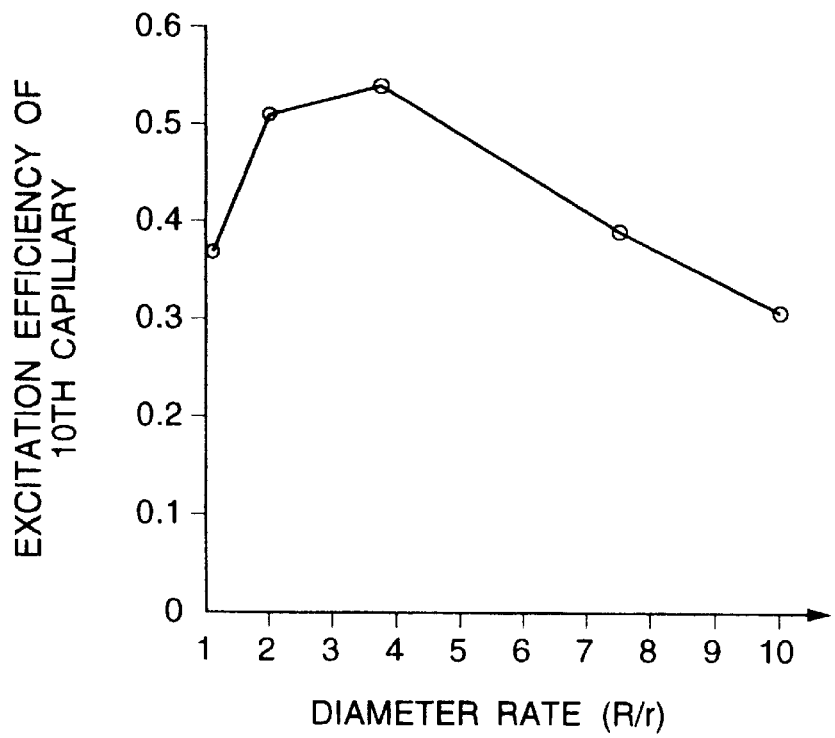
FIG. 7 is a graph showing the relation between the ratio of outside diameter to inside diameter of a capillary and excitation efficiency in Example 1 of the present invention.

As another example, in a case where the inside diameter of a capillary was 0.1 mm (r=0.05 mm), and the outside diameters were 0.11 mm (R=0.055 mm), 0.2 mm (R=0.1 mm), 0.375 mm (R=0.75 mm), 0.75 mm (R=0.375 mm) and 1.0 mm (R=0.5 mm), a calculation similar to the above was performed (with other conditions being the same as above). The array pitches of the ten capillaries were made to agree with the outside diameter of each capillary, and each capillary was aligned in a close-pack configuration. FIG. 7 represents the change of the excitation efficiency in the tenth capillary aligned at the farthest position from the laser source according to the o.d./i.d. ratio (R/r) of the capillary (the excitation efficiency is normalized by the excitation efficiency in the first capillary on the laser source side in each ratio, in a similar manner as in FIG. 6). In this calculation demonstration, the inside diameters of the capillaries are unified to 0.1 mm, but also in cases where capillaries with other inside diameters are used, essentially the same results are obtained if they have the same o.d./i.d. ratio (R/r) of the capillary (wherein the width of the incident laser beam is much the same as the inside diameter of the capillary).

Figure 8:
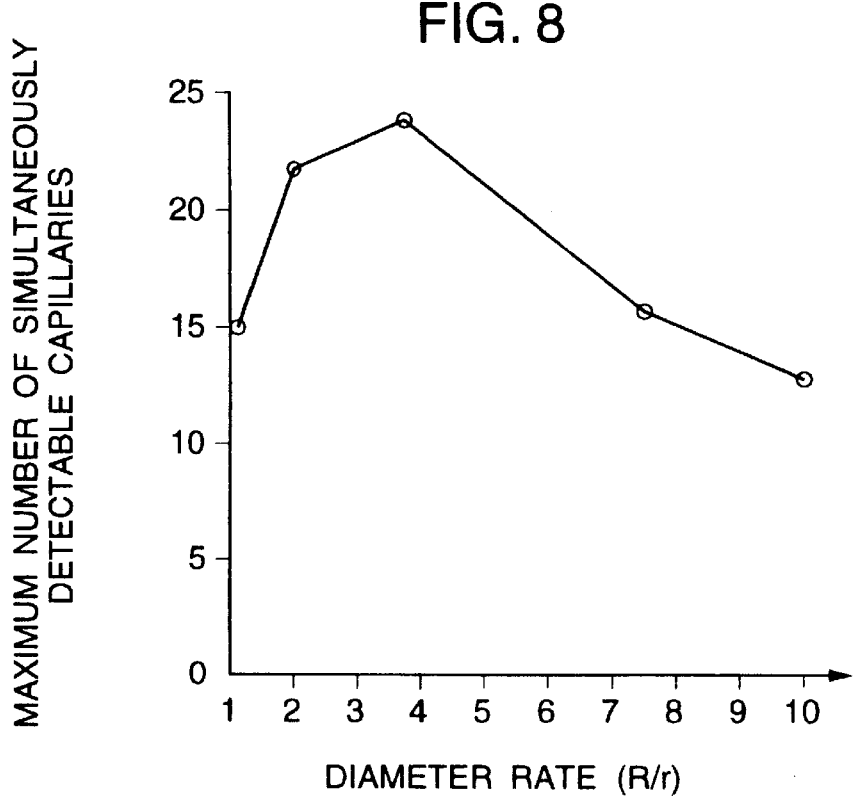
FIG. 8 is a graph showing the relation between the ratio of outside diameter to inside diameter of a capillary and the number of capillaries in which samples can be detected at the same time in Example 1 of the present invention.

FIG. 8 shows the results of the calculation of the maximum number of simultaneously detectable capillaries in a similar manner as above, where the mean transmittance of the laser beam per capillary was calculated from the results of FIG. 7 and the decrease of the excitation efficiency was assumed up to 20%. It was revealed from the results of FIGS. 7 and 8 that the most efficient simultaneous detection of a plurality of capillaries was allowed when R/r, i.e. the ratio of o.d./i.d. equaled a value around 4 (accurately, 3.75), and the number of the capillaries that were simultaneously detectable decreases as the ratio deviates from the value. The capillaries simultaneously detectable decreased when the ratio of o.d./i.d. was low because there were such beam components that deviated from the outside diameter of the capillaries, for the laser beam width and the value of the outside diameter of the capillaries were close to each other. The capillaries that were simultaneously detectable decreased when the ratio of o.d./i.d. was high because there were such beam components that transmitted the glass part of the capillaries without transmitting the inside of the capillaries.

Generally a microtiter plate is widely used when a large amount and various different samples for analysis or sequencing are prepared and processed. The microtiter plate is a plate with 96 wells arranged in a 12×8 grid, which is a worldwide standard. Thus to make the numbers of the samples to be analyzed by electrophoretic detection at the same time a multiple of 8 or 12 is quite important in linking a large-scale sample preparation and electrophoretic detection. In other words, the numbers of the samples to prepare and detect at the same time are preferably 8, 12, 16, 24, - - - . From the results in FIG. 8, the conditions of the ratio R/r of the o.d./i.d. of capillaries for allowing the simultaneous detection in which the decrease of excitation efficiency in each capillary is up to 20% when the numbers of the samples to prepare and detect at the same time are 8, 12, 16, 24 are respectively $1<R/r\leq10$, $1<R/r\leq10$, $1<R/r\leq7$ and $3\leq R/r\leq5$.

Next the condition to reduce the background light due to the scattering of a laser beam, which is another point of the present invention, is described. The scattering of a laser beam is mainly caused by the reflection of the laser beam at a boundary where the refractive index changes. The reflected light proceeds to a direction in which the incident angle and the reflection angle are equal, following the law of reflection. As a result, the reflected light proceeds in a variety of directions, and some goes into the light detecting system aligned toward a direction perpendicular to the capillary array plane. This considerably increases the background light during fluorescence detection, leading to reduction of the fluorescence detection sensitivity. The laser power of the reflected light that goes directly into the light detection system can be totaled with all the capillaries to estimate the influence.

Figure 9:
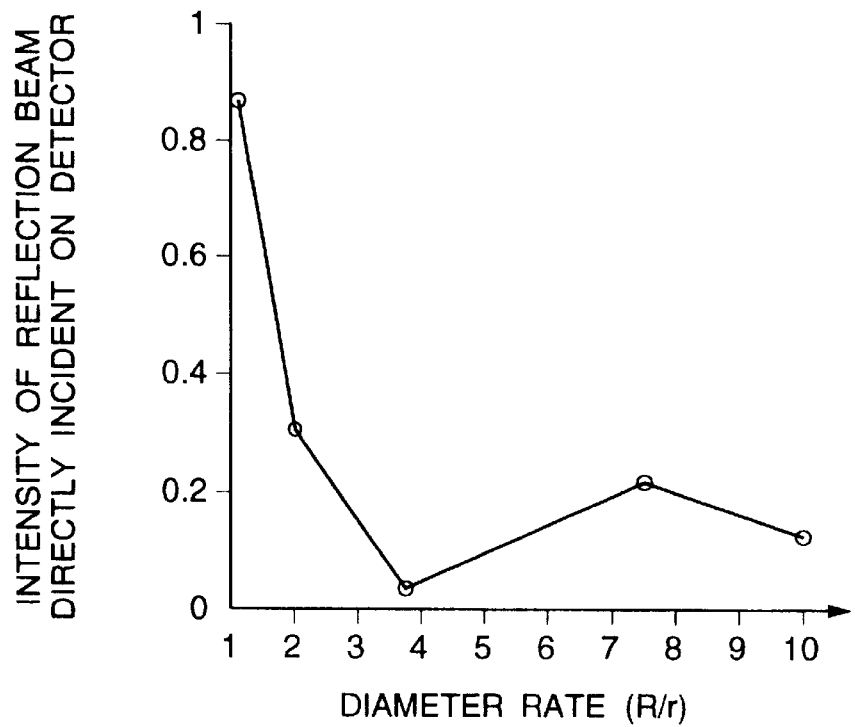
FIG. 9 is a graph showing the relation between the ratio of outside diameter to inside diameter of a capillary and the calculation result of the intensity of reflected light directly coming into the optical detection system in Example 1 of the present invention.

FIG. 9 shows the change of the results of totaling the laser power of the reflected light that directly goes into the light detection system according to the o.d./i.d. ratio (R/r) of capillaries, with similar calculation demonstration conditions for obtaining the results of FIGS. 7 and 8 above. The laser power of the reflected light that directly goes into the light detection system, as stated above, greatly increases the background light during fluorescence detection, leading to the reduction of detection sensitivity. Therefore, the smaller the value is, the higher the sensitivity of fluorescence detection becomes. From the results in FIG. 9, the ratio R/r around 4 provided the least background light and the highest sensitive fluorescence detection, and as the ratio deviated from the value, the background light increased and the sensitivity of fluorescence detection lowered. The background light greatly increased when the ratio of o.d./i.d. was low because the percentage of such beam components that are irradiated with a large incident angle increased. It was revealed from the results above that the condition of $2\leq R/r$ is effective for a highly sensitive detection of fluorescence.

Reducing the reflectance at each boundary where a refractive index changes leads to reducing the laser power of the reflected light that directly goes into the optical detection system. To reduce the reflectance, the outside of the capillary at the position a laser irradiates may be filled with a transparent liquid such as water or an aqueous solution, etc., as described in the fifth example under BACKGROUND OF THE INVENTION. At this time, however, the angle of refraction becomes larger at the same time as evident from Equation 9. In other words, each capillary acts as a concave lens and it is disadvantageous for making laser power reach to many capillaries. The conditions therefore should be evaluated with the balance of these considerations. As a result of simulation, filling the outside of the capillary with $R/r\leq2$ provided more effect of reducing the background light. Consequently, many capillaries can be simultaneously analyzed in an array, realizing a high-speed, high-throughput and high-sensitivity analysis. The use of a cylindrical capillary with a size other than those used in this example shall, of course, give a similar effect.

Example 2

In Example 1, the capillaries aligned in a plane feature were placed in a close pack configuration, while here the pitch between adjacent capillaries was made equal to, or more than the outside diameter of the capillaries. As an example, ten fused silica capillaries (cylindrical tubes) ($n_2$= 1.46) with an outside diameter of 0.2 mm (R=0.1 mm) an inside diameter of 0.1 mm (r=0.05 mm), and a length of 50 cm were used. The investigated array pitches were once (same as Example 1), twice, three times, four times and five times as large as the outside diameter of the capillary, i.e. 0.2, 0.4, 0.6, 0.8 and 1.0 mm. The other experimental conditions were made the same as those in Example 1.

Figure 10:
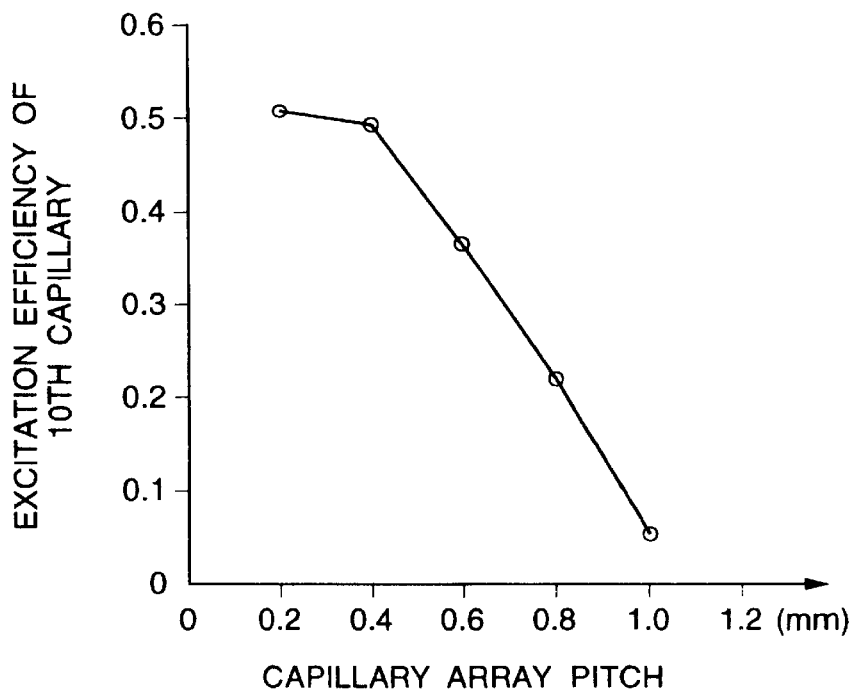
FIG. 10 is a graph showing the relation between the capillary array pitch and excitation efficiency in Example 2 of the present invention.

FIG. 10 shows the excitation efficiency in the tenth capillary aligned at a position most distant from a laser source, making the array pitch of the capillary as a variable (similar to FIG. 6, the excitation efficiency was normalized by the excitation efficiency in the first capillary aligned at a position closest to the laser source). From the result in FIG. 10, the excitation efficiency in the tenth capillary decreased with the increase of the array pitch of the capillaries, which became a disadvantageous condition for simultaneous detection of a lot of capillaries. In other words, it was revealed that simultaneous detection of a lot of capillaries can be performed with highest efficiency when the array pitch is made to agree with the outside diameter of the capillary, i.e. the capillaries are arranged in a close pack configuration. Assuming that the condition with which the S/N of the tenth capillary is more than half of the S/N of the tenth capillary in this optimal condition (capillaries are arranged in a close pack configuration) is a practical range, the condition with which the excitation efficiency of the tenth capillary is more than ¼ of that in the optimal condition is practical. The condition with which the excitation efficiency is more than ¼ is satisfied, from FIG. 10, if the array pitch of the capillaries is 0.8 mm or shorter, that is, the array pitch is equal to, or less than four times as large as the outside diameter of the capillary.

Example 3

Figure 11:
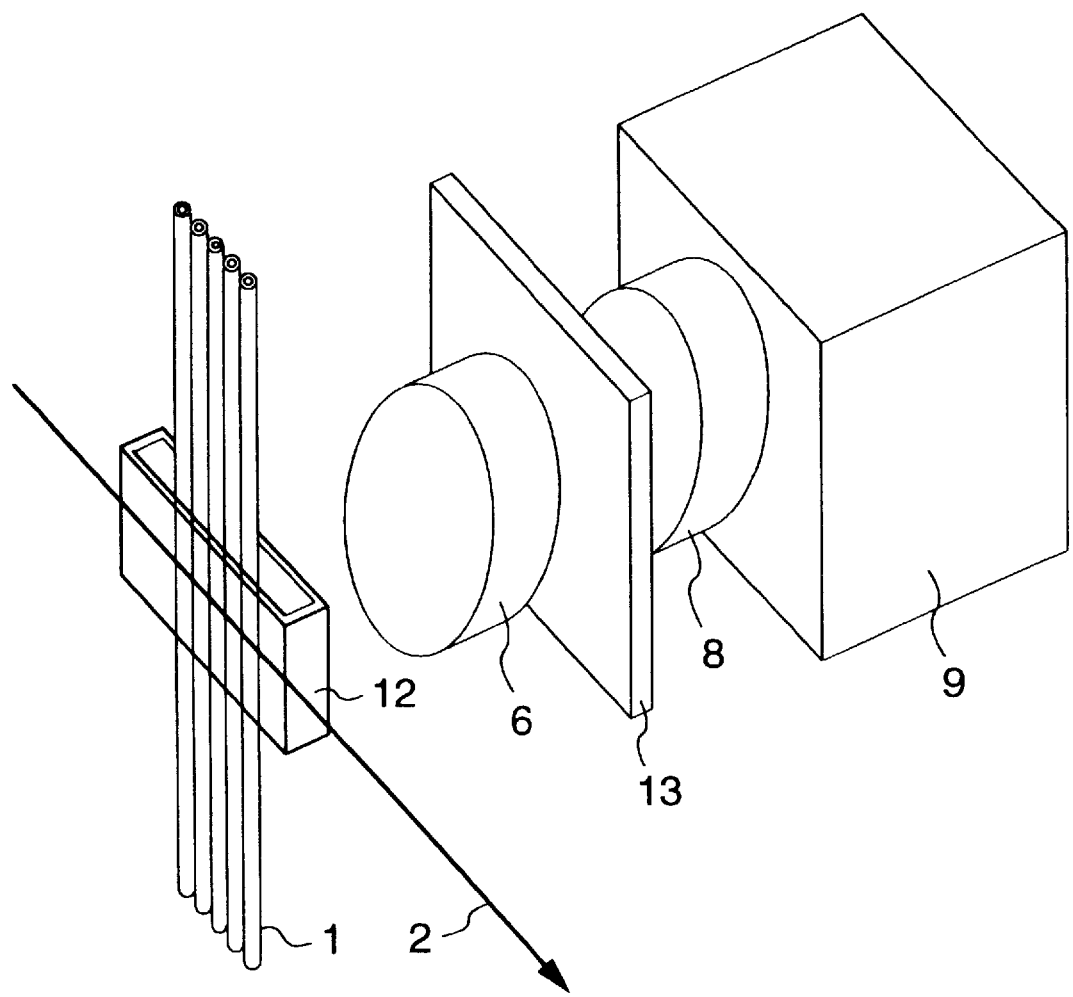
FIG. 11 is a diagram illustrating the major construction of the system in Example 3 of the present invention.

Based on the results of simulation in Example 1, DNA samples were actually electrophoresed in this example. In the first place, electrophoresis was performed using five capillary gels arranged in a plane feature, the part of the capillary gel to detect fluorescence was placed in water, and fluorescence was detected to perform DNA sequencing. FIG. 11 shows the basic construction of the system used. A capillary gel was prepared by injecting an acrylamide solution of concentrations 4% T (total monomer concentration) and 5% C (crosslinking material concentration) containing 7M urea as a denaturing agent into a fused silica 5 cylinder that was 50 cm long, and had an outside diameter of 0.2 mm (R=0.1 mm) and an inside diameter of 0.1 mm (r=0.05 mm) ($n_2$=1.46), then allowing it to gel ($n_3$=1.36). A window to detect fluorescence had been preliminarily formed as a laser irradiation site by removing the polyimide coating with 10 mm length all around each capillary at a position 30 cm from the sample injection end of the capillary. As shown in FIG. 11, five of the capillary gels were aligned in a plane feature with a uniform pitch of 0.2 mm, and fixed in a fluorescence detection cell 12 filled with water ($n_1$=1.33). In FIG. 11, the capillary gels are shown with only the neighborhood of the detection windows on the capillary gels.

Figure 12:
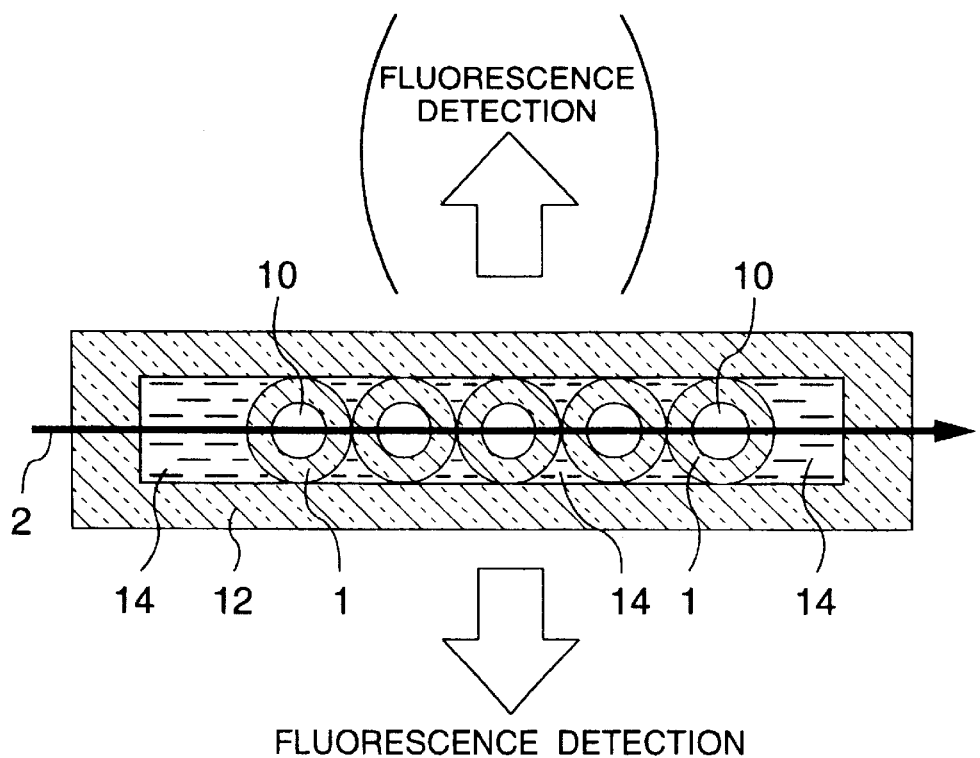
FIG. 12 is a cross-sectional view of the part where fluorescence is detected in Example 3 of the present invention.

FIG. 12 shows a cross-sectional view cutting the capillary axis of a fluorescence detection cell 12. After a YAG laser (532 nm, 20 mW) and a He-Ne laser (594 nm, 10 mW) were made coaxial, they were focused to have 0.1 mm of a beam diameter to make a beam 2, and they were made to go from the side of the capillary array along the capillary array axis. Inside the fluorescence detection cell 12, capillaries 1 filled with acrylamide 10 were aligned on a plane and the outside of the capillaries 1 were filled with water 14. From the inside diameter, outside diameter and the refractive index of each medium, based on Equation 18 below, $\Delta\theta$=1.73° was calculated, each capillary had a concave lens action, satisfying Equation 20 but not Equation 22 both of which are described below.

As shown in FIG. 11, the fluorescence detection was performed from a direction perpendicular to the capillary gel alignment plane. The lights from a group of five light sources from five capillaries aligned in a row with 0.8 mm width in the horizontal direction were made to have substantially parallel luminous flux, made to transmit an image-splitting prism which splits the image of the fluorescent light source group into four in the vertical direction, and four combined filters 13 matched with the luminous flux which formed the four images, and the images were formed by the second camera lens 8. This fluorescence selection method is described in detail by Japanese Patent Application Laid-Open No. 2-269936. The fluorescent light source group developed in a two-dimensional feature with 5×4=20 was detected at one time with exposure detection by a two-dimensional CCD camera 9. The detection was continuously performed with 1.0 second of exposure time and 1.5 second of data acquisition interval.

Five different DNA samples were sequenced by the Sanger's sequencing method. The prepared DNA sample components were labeled with four different fluorophores: Cy3 (maximum emission wavelength: 565 nm), TRITC (maximum emission wavelength: 580 nm), Texas Red (maximum emission wavelength: 615 nm), and Cy5 (maximum emission wavelength: 665 nm), which correspond to terminal base species C, G, A and T. Cy3 and Cy5 are available from Biological Detection System (USA), and TRITC and Texas Red are available from Molecular Probes, Inc. Four different combined filters were used for wavelength selection and image formation of the four different fluorescent lights. Four different reactants corresponding to terminal base species were mixed with every sample species, then they were concentrated to 10-fold by ethanol precipitation and the sample medium was displaced with formamide. The sample injection ends of five capillary gels were respectively immersed into five different DNA sample solutions, and the samples were injected by applying 100 V/cm (5 kV) of a constant electric field strength for two seconds on both ends of five capillary gels. Electrophoresis was performed at 100 V/cm (5 kV) with a constant electric field strength for about three hours. The time course of four different signals corresponding to the four different fluorescent lights obtained by the two-dimensional CCD camera was analyzed and the DNA sequence of the five different samples were determined.

Figure 13:
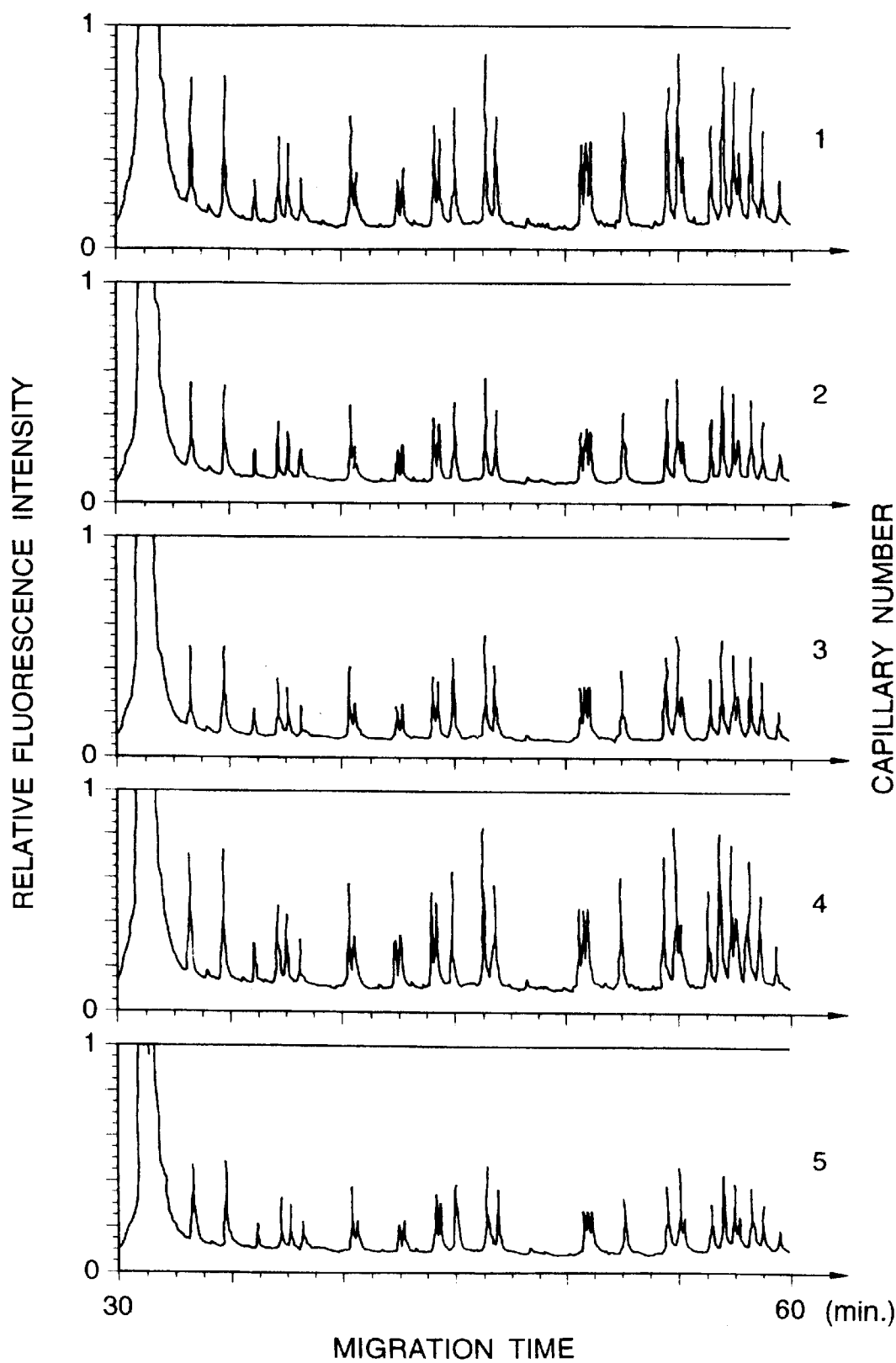
FIG. 13 shows examples of electrophoresis migration patterns obtained in Example 3 of the present invention.

FIG. 13 shows the electrophoretic pattern of A-terminated fragments with Texas Red, with the migration time 30 to 60 minutes, up to ca. 130 bases from the primer, out of the DNA sequencing results obtained in this example. All the five different analyzed samples are M13mp18, the standard sample. The capillary −1 with the top column of FIG. 13 is the capillary closest to the laser source, and the electrophoretic patterns of the capillary in positions farther from the laser source in the number order are shown. The peak intensity decreased as the capillary was placed farther from the laser source. The peak intensity of the capillary −5 was ⅓ of that of the capillary −1, yet the peaks were detectable with sufficiently high S/N (S/N=734 at the position corresponding to base length 91). The S/N on the peaks of the capillary −1 is S/N=3300 at a position corresponding to base length 91.

In this experimental condition, the medium outside of the capillary at the position of laser irradiation is water. Therefore the laser reflection at the capillary surface decreased and the background light signal decreased by almost one order as compared with the case where the outside medium is air. This means that the description in Example 1 has been experimentally proved. The electrophoretic patterns of other fluorescently-labeled components were obtained similarly, and the DNA sequencing with a five-capillary gel electrophoresis was realized with high sensitivity.

Then ten capillary gels aligned in a plane feature were placed in air and electrophoresed, and DNA sequencing was performed by detecting the fluorescence from the migrating sample components. The capillary used was a fused silica cylindrical tube ($n_2$=1.46) with an outside diameter of 0.375 mm (R=0.1875 mm) and an inside diameter of 0.1 mm (r=0.05 mm). Ten capillaries were arranged on a glass plane, fixed with 0.375 mm pitch as shown in FIG. 4, without using the fluorescence detection cell shown in FIGS. 11 and 12. Thus the medium outside of the capillary is air ($n_1$=1.00). Other conditions were the same as the previous experiment. From the inside diameter, outside diameter and the refractive index of each medium, based on Equation 18 below, $\Delta\theta$=−0.54° was calculated; each capillary thus had a convex lens action, satisfying both Equations 20 and 22 described below.

Figure 14:
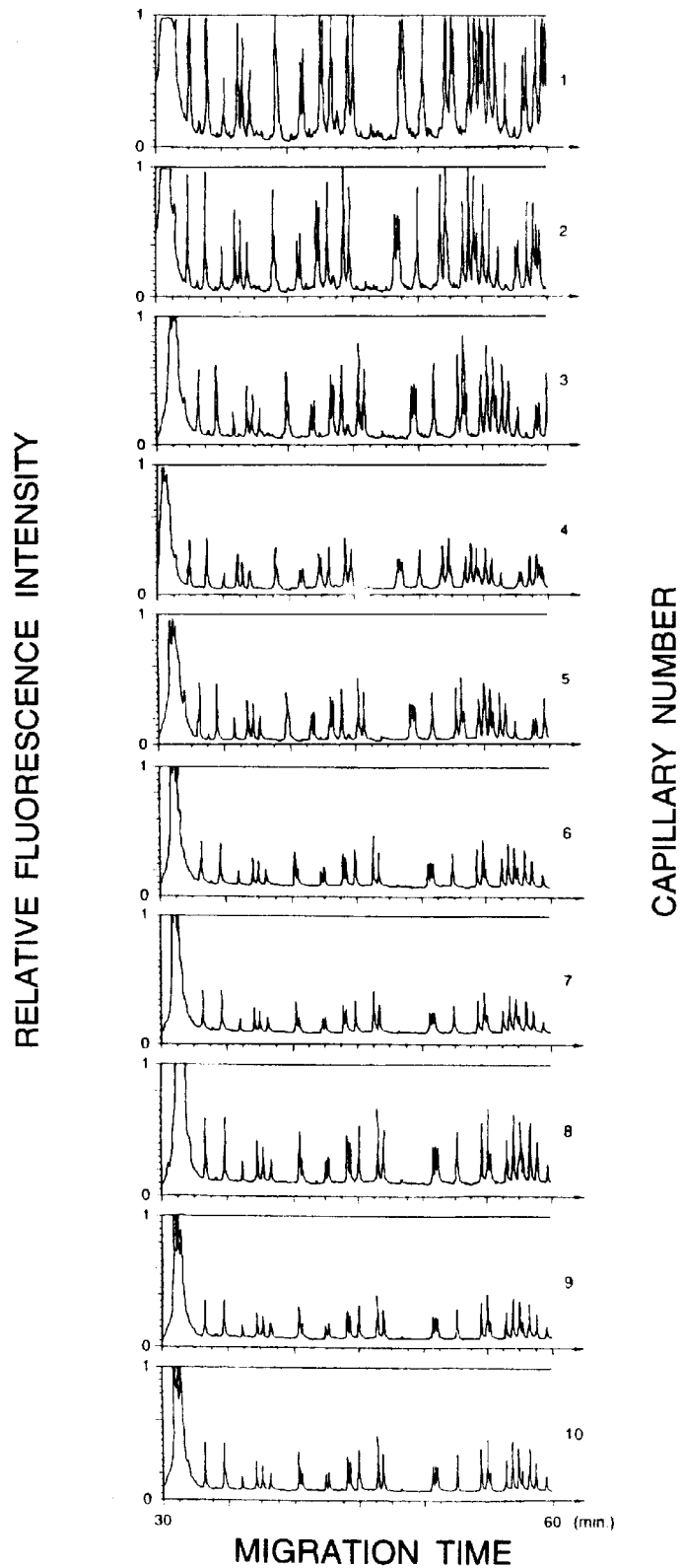
FIG. 14 is an electropherogram showing an example of the electrophoresis migration pattern obtained in Example 3 of the present invention.

FIG. 14 shows the electrophoretic pattern of A-terminated fragments with Texas Red, with the migration time 30 to 60 minutes, up to ca. 100 bases from the primer, out of the DNA sequencing results obtained in this example. All ten different analyzed samples are M13mp18, the standard sample. In FIG. 14, the capillary −1 at the top is the capillary closest to the laser source, and the electrophoretic patterns of the capillary in positions farther from the laser source in number order are shown. Any of the ten capillaries including the capillary −10 at the bottom allowed detection with sufficient S/N. In the peak at 9 bases, S/Ns were 237 at capillary −1, 237 at capillary −4, 110 at capillary −7, and 140 at capillary −10 (The reason the S/N at capillary −10 was larger than the S/N at capillary −7 is thought to be dispersion of the detection). The electrophoretic patterns of other fluorescently-labeled components were obtained similarly as in FIG. 14, and the DNA sequencing with a ten-capillary gel electrophoresis was realized with high sensitivity.

Example 4

In this example, the tubular capillaries have elliptical cross section. By using these capillaries, two different effects are generated according to the arrangement method. The first method is to parallel the minor axis with the capillary array plane. This case provides a smaller incidence angle of the laser beam than the case where a cylindrical capillary is used, therefore the laser power of the reflected light which directly goes into the optical detection system is reduced and the background light signal is decreased. This provides the effect of increasing the fluorescence detection sensitivity. The second arrangement method is to parallel the major axis with the capillary array plane. In this case, the pitch between the migration paths of adjacent capillaries (inside of the capillaries) can be enlarged while the capillaries are arranged in a close pack configuration, therefore mutual crosstalks disappear and it is advantageous for individual detection of a plurality of capillaries. Next, an embodiment using the first arrangement method is shown.

As an embodiment, an elliptic capillary was used which, in cross section, had an outer major axis of 0.75 mm (outer semi-major axis $R_1$=0.375 mm), an outer minor axis of 0.1875 mm (outer semi-minor axis $R_2$=0.09375 mm), an inner major axis of 0.2 mm (inner semi-major axis $r_1$=0.1 mm) and an inner minor axis of 0.05 mm (inner semi-minor axis $r_2$=0.025 mm). The area of the inside of the capillary cross section equals to the area of the inside of the cross section of a cylindrical capillary with an outside diameter of 0.375 mm (R=0.1875 mm) and an inside diameter of 0.1 mm (r=0.05 mm) ($7.85\times10^{-3}$ mm$^2$). The capillary of this form can be manufactured by Polymicro Technologies, Inc. The other experimental conditions are the same as those in Example 1, using fused silica ($n_2$=1.46) for the material of the capillary of 50 cm overall length, and the inside of the capillary was filled with acrylamide gel ($n_3$=1.36) of 4% T and 5% C of the concentration containing 7M urea. A window to detect fluorescence had been preliminarily formed as a laser irradiation site by removing the polyimide coating along 10 mm of length all around each capillary at a position 30 cm from the sample injection end of the capillary.

The sites for detecting fluorescence of the ten capillary gels were arranged in a manner similar to those in FIGS. 3 and 4, when the minor axes of the ellipse of all the capillaries were paralleled with the array plane of the capillaries and the major axes were set perpendicular to the array plane of the capillaries. This arrangement method has an effect for reducing the reflected light which directly comes into the light detection system described above. The capillary array pitch was made to agree with the outer minor axis of the ellipse, arranged in a close-pack configuration. The outside of the capillary at a fluorescence detection site was air ($n_1$=1.00). Similar to FIG. 3, the fluorescence detection was performed with a two-dimensional detector from the direction perpendicular to the capillary array plane via the first lens, a bandpass filter and the second lens. The laser was focused to a beam diameter of 0.1 mm and made to go from the side of a capillary array along the capillary array axis.

Figure 15:
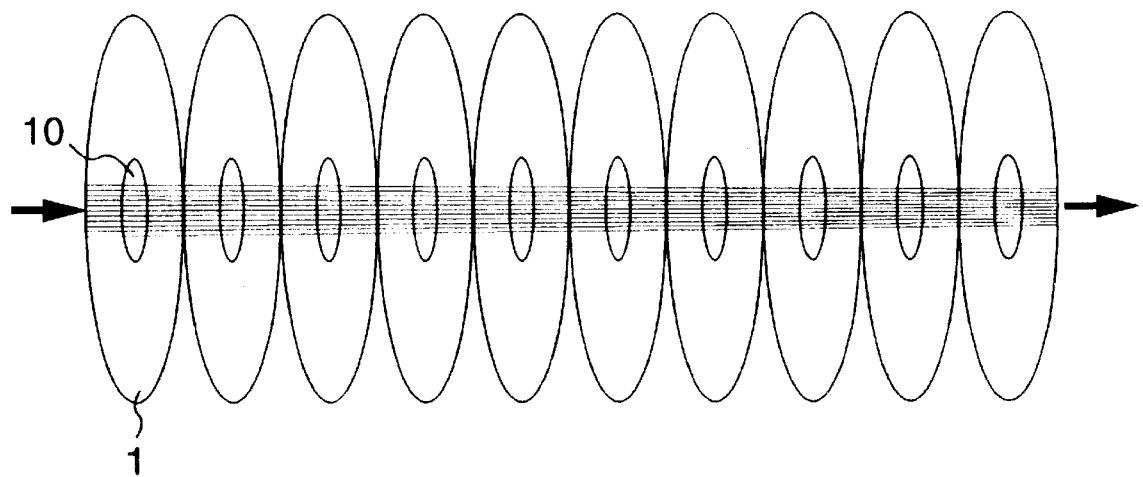
FIG. 15 is a diagram illustrating the simulation result of the optical path in the capillary array in Example 4 of the present invention.

With these experimental conditions, a simulation demonstration similar to Example 1 was performed. FIG. 15 is a result of calculation of optical paths of eleven beam components. FIG. 15 is a cross-sectional view of a fluorescence detection site cutting the capillary axis, the left capillary being the capillary closest to the laser source, and the capillary to the right being farther from the laser source. Calculation of all the paths was continuously performed on the assumption that ten capillaries were arranged as stated above. With these simulation conditions, the angle of refraction of the laser beam by a capillary $\Delta\theta$=ca. 0, in other words, the lens action of the capillary was weak, therefore each beam component proceeded in the capillary array without a great refraction. It was revealed that all the beam components transmit the inside of all the ten capillaries without deviating to the outside of the capillaries and contribute to excitation of the sample components migrating in the capillaries.

Similar to FIG. 6, the length of the optical path (optical path length) of the light beam transmitting the inside of capillaries was calculated for each capillary, the optical path length was multiplied by the laser power at the position, and the results for all capillaries were totaled to obtain an excitation efficiency, for the purpose of evaluating the change of the degree of the excitation efficiency decrease with the number of the capillaries.

Figure 16:
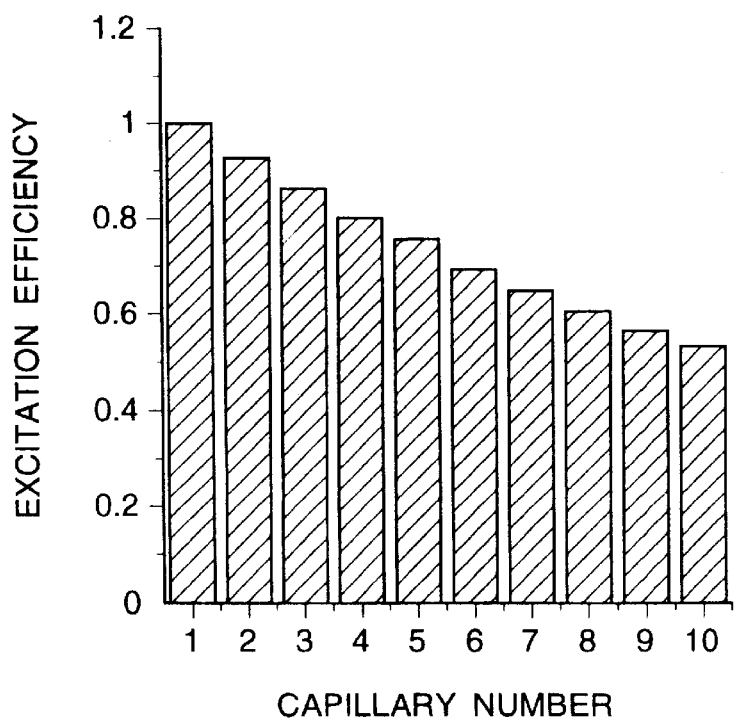
FIG. 16 is a graph showing the relation between the position of the capillaries and excitation efficiency in Example 4 of the present invention.

FIG. 16 shows the excitation efficiency in each capillary obtained in this way (normalized by the value of the capillary closest to the laser source). In FIG. 16, each capillary was numbered from 1 to 10 in order from the laser source side. Similar to FIG. 6, the excitation efficiency of every capillary decreased exponentially as the capillary was placed farther from the laser source. The excitation efficiency of the tenth capillary was as high as 53.4% of the first one, and the degree of attenuation was nearly equal to the case of FIG. 6. That is, the mean transmittance for a capillary was 93.3% ($0.933^9\approx0.536$), and simultaneous detection of capillaries up to 24 was possible ($0.933^{23}\approx0.20$).

On the other hand, the total laser power of the reflected light that directly went into the light detection system for the ten capillaries was zero, different from the case of Example 1. The reason for this was that the incidence angle of the laser beam at each boundary where refractive indexes change became sufficiently small. It was therefore revealed that the background light can be greatly reduced and fluorescence can be detected with higher sensitivity by using an elliptical tubular capillary instead of a cylindrical capillary.

The use of an elliptical tubular capillary with forms and dimensions other than those used in this example provides similar effects. Moreover, as shown with cylindrical capillaries in Examples 1 and 3, the effect of disposing the capillary at the laser irradiation site in a transparent liquid such as water, etc. is similarly obtained also with an elliptical tubular capillary. In other words, the reflectance of the laser beam which goes into a capillary is reduced and a plurality of capillaries can be efficiently detected at the same time.

17

Example 5

In this example, a simulation was performed with the experimental conditions of Example 4, the laser irradiation site of each capillary being treated with an antireflection coating. Before filling acrylamide gel, magnesium fluoride ($MgF_2$) (refractive index $n_0=1.38$) was deposited in a single layer with 184 nm of thickness on the window (part where coating is removed) of an elliptic tubular capillary for detection of fluorescence. This treatment increased the mean transmittance of the laser beam per capillary gel from 93.3% to 97.0%, when the excitation efficiency in the tenth capillary increased from 53.4% to 76.0% ($0.970^9 \approx 0.76$). Attending this, the maximum number of capillaries which allow simultaneous detection limiting the decrease of excitation efficiency to 20% increased from 24 to 53 ($0.970^{52} \approx 0.21$). Application of the treatment of the laser irradiation site of each capillary with antireflection coating used in this example to the cylindrical capillary described in Example 1 or a capillary in a square tubular shape described below in Example 6 of course leads to similar effects. The methods and kinds of coating shall not be 5 limited to those used in this example.

Example 6

Figure 17:
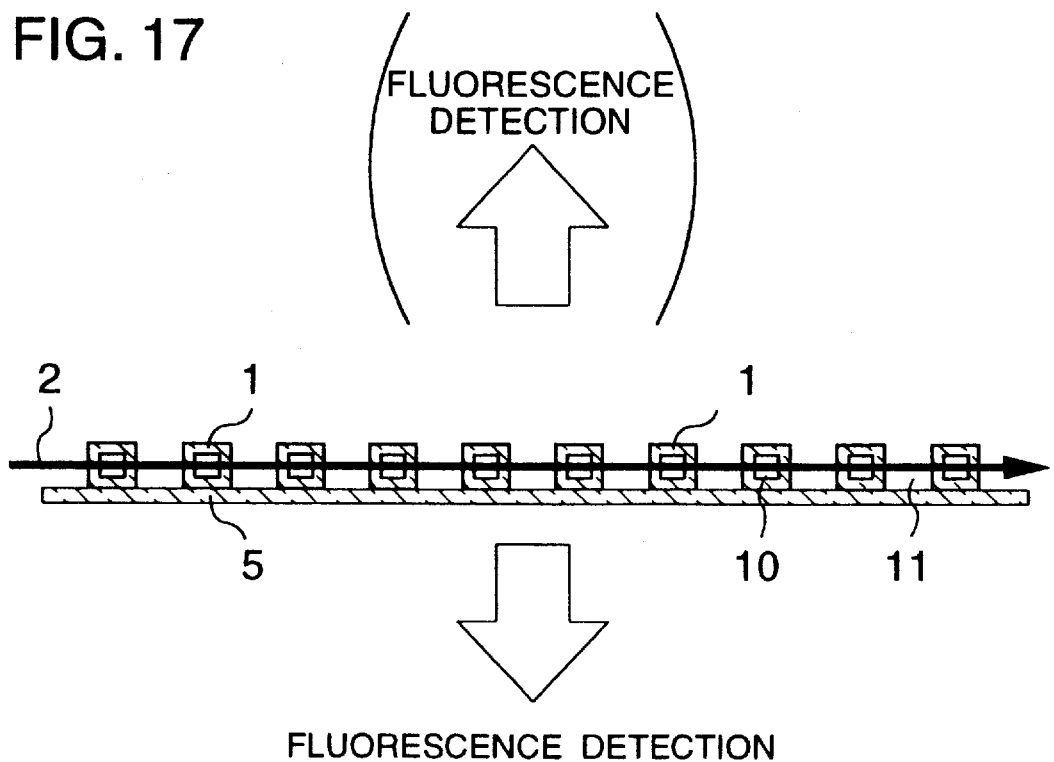
FIG. 17 is a cross-sectional view of the part where fluorescence is detected in Example 6 of the present invention.

In this example, a square tubular shape capillary 1 as shown in FIG. 17 was used. The cross section of the square tubular shape capillary had an outside perimeter of a square with an edge of 0.2 mm and an inside perimeter of a square with an edge of 0.1 mm. The capillary of this shape can be manufactured by Polymicro Technologies, Inc. (U.S.). The other experimental conditions were the same as those in Example 1, using fused silica ($n_2=1.46$) for the material of the capillary of 50 cm overall length, and the inside of the capillary was filled with acrylamide gel ($n_3=1.36$) of 4% T and 5% C of the concentration containing 7M urea. A window to detect fluorescence had been preliminarily formed as a laser irradiation site by removing the polyimide coating from 10 mm of the length all around each capillary at a position 30 cm from the sample injection end of the capillary. The detection parts of 10 capillary gels were made all of uniform pitch of 0.4 mm, and respective capillaries were arranged in a plane feature fixed on a glass plate 5. The outside of the capillary at the fluorescence detection was air ($n_1=1.00$) 11. Like FIG. 3, the fluorescence detection was performed with a two-dimensional detector from the direction perpendicular to the capillary array plane via the first lens, a band pass filter and the second lens. FIG. 17 is a cross-sectional view cutting the capillary axis of the fluorescence detection site. A laser was focused to a beam diameter of 0.1 mm and made to go into the capillary from the side of the capillary array along the capillary array axis as a beam 2.

With the conditions of this simulation, the influence of refraction of a laser can be neglected because the angle of incidence into each capillary is always zero. The mean transmittance of the laser beam per capillary was 92.9%, considering the influence of reflection at each boundary where refractive indexes change, and the excitation efficiency in the tenth capillary from the laser source was 51.5% of the excitation efficiency in the first capillary ($0.929^9 \approx 0.515$). It was revealed that simultaneous detection of up to 22 capillaries is possible ($0.929^{21} \approx 0.21$) with the simulation conditions, assuming that the decrease of the excitation efficiency that allows simultaneous detection is limited to 20% based on the relation between the sensitivity of the detector and the dynamic range.

18

On the other hand, the result of totaling the laser power of the reflected light that directly comes into the light detection system having ten capillaries was zero, like the case of Example 4. The reason for this is that the incidence angle of the laser beam at each boundary where refractive indexes change is always zero. Therefore the background light can be greatly reduced and fluorescence can be detected with a higher sensitivity by exchanging a cylindrical capillary for a square tubular capillary.

Example 7

In this example, the simulation conditions of Example 6 were partially altered by making the outside of the capillary at the fluorescence detection site be water ($n_1=1.33$). The other simulation conditions were the same as those of Example 6. With these simulation conditions, the difference between the refractive index of the outside of a capillary and the refractive index of the capillary became smaller than that in Example 6, and therefore the reflectance of the laser beam at each boundary where refractive indexes change greatly decreased. As a result, the mean transmittance of the laser beam per capillary increased from 92.9% to 99.3%, when the excitation efficiency in the tenth capillary increased from 51.5% to 93.9% ($0.993^9 \approx 0.939$). Attending this, the maximum number of capillaries which allow simultaneous detection limiting the decrease of excitation efficiency to 20% increased from 22 to 230 to ($0.9932^{29} \approx 0.20$).

Next, the simulation conditions of Example 6 were partially altered by making the outside of the capillary at the fluorescence detection site be quartz glass ($n_1=1.46$). These simulation conditions may be realized by welding the detection sites of a plurality of the square tubular capillaries or by preparing a plurality of holes corresponding to the inside of the capillaries on the block of quartz glass. Similar effects are also obtained by filling the outside of the capillaries with a transparent liquid, e.g. glycerol ($n_1=1.47$). The other simulation conditions were made the same as those in Example 6. With these simulation conditions, the difference between the refractive index of the outside of a capillary and the refractive index of the capillary became smaller than that in Example 6, and therefore the reflectance of the laser beam at each boundary where refractive indexes change greatly decreased. As a result, the mean transmittance of the laser beam per capillary increased from 92.9% to 99.8%, when the excitation efficiency in the tenth capillary increased from 51.5% to 98.2% ($0.998^9 \approx 0.982$). Attending this, the maximum number of capillaries which allow simultaneous detection limiting the decrease of excitation efficiency to 20% increased from 26 to 804 ($0.998^{803} \approx 0.20$). In this example, the outside of the capillary at the fluorescence detection site was filled with water or quartz glass, but other transparent materials, of liquid or solid, have similar effects. Example 8

Figure 18:
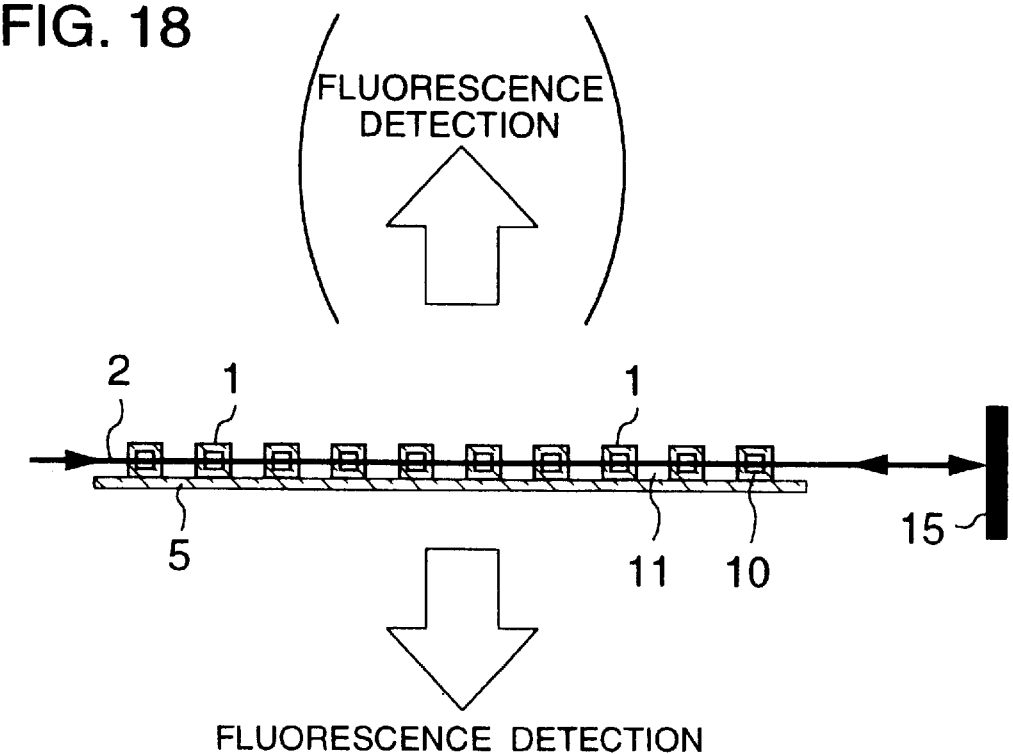
FIG. 18 is a cross-sectional view of the part where fluorescence is detected in Example 8 of the present invention.

In this example, with the experimental conditions of Example 6, as shown in FIG. 18, a total reflection mirror 15 was placed at the position where a laser beam 2 transmitted ten capillaries, and the laser beam 2 was reflected to transmit the ten capillaries through the reverse path. The other conditions were made the same as those in Example 6.

When N capillaries are aligned, the excitation efficiency $T_{eff}$ in the nth capillary from a laser source is represented by Equation 12 if the mean transmittance of the laser beam per capillary is $T_{ram}$ ($X \uparrow (Y)$ represents the Yth power of X in the following description):

$$T_{eff} = T_{ram} \uparrow (n-1) + T_{ram} \uparrow (2N-n) \qquad \text{(Equation 12)}$$

The first term of Equation 12 represents the excitation by the laser beam proceeding in a direction leaving the laser source, and the second term represents the excitation by the laser beam proceeding in a direction approaching the laser source after being reflected by the total reflection mirror 15. Equation 12 is normalized by the excitation efficiency at the first capillary in the case of Example 6, and $T_{eff} > 1$ means that this excitation efficiency is more than the excitation efficiency at the first capillary in the case of Example 6. According to Equation 12, the excitation efficiency $T_{eff}$ simply decreases with n as is the case with Example 4, and becomes minimum when n=N, i.e. at the capillary farthest from the laser source. The excitation efficiency at this time $T_{effmin}$ is Equation 13:

$$T_{effmin} = T_{ram}\uparrow(N-1) + T_{ram}\uparrow(N) \quad \text{(Equation 13)}$$

Equation 13 means that the excitation efficiency in the Nth capillary is about twice as large as the case of Example 6, that is the case where no total reflection mirror is used. With these simulation conditions, N=10 and $T_{ram}=0.929$, therefore the excitation efficiency in the tenth capillary increased from 51.5% to 99.4% ($0.929^9 + 0.929^{10} \approx 0.994$). Attending this, the maximum number of capillaries which allow simultaneous detection limiting the decrease of excitation efficiency to 20% increased from 22 to 32 ($0.929^{31} + 0.929^{32} 0.20$). It is natural that the application of the technique shown in this example to a cylindrical capillary or an elliptic tubular capillary provides similar effects.

Example 9

Figure 19:
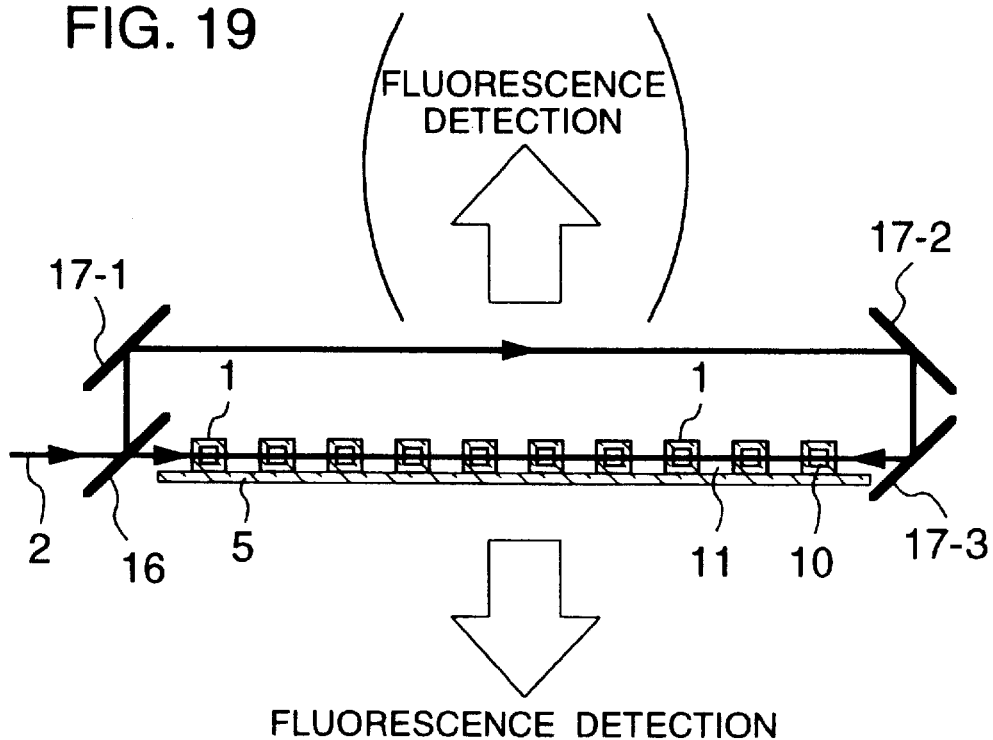
FIG. 19 is a cross-sectional view of the part where fluorescence is detected in Example 9 of the present invention.

In this example, wit h the experimental conditions of Example 6, as shown in FIG. 19, a laser beam 2 (either laser light of a single wavelength, or laser light prepared by mixing light having a plurality of wavelengths from a plurality of laser sources and making them coaxial) was split into two with a beam splitter such as a half mirror 16, etc., then it was made to irradiate from both the two sides of the capillary array plane in which ten capillaries were aligned, using reflection mirrors 17-1, 17-2 and 17-3. Both of the laser beams irradiating from the sides were focused to 0.1 mm of a beam diameter with lenses (not shown), and were adjusted to be coaxial with each other. The other simulation conditions were made the same as those in Example 6. When N capillaries are aligned in a plane, the excitation efficiency $T_{eff}$ in the nth capillary from one side is represented by Equation 14 if the mean transmittance of the laser beam per capillary is $T_{ram}$:

$$T_{eff} = \tfrac{1}{2} T_{ram}\uparrow(n-1) + \tfrac{1}{2} T_{ram}\uparrow(N-n) \quad \text{(Equation 14)}$$

The first and second terms of Equation 14 represent the excitations by the two split laser beams, respectively. Equation 14 is normalized by the excitation efficiency at the first capillary in the case of Example 6. According to Equation 14, the excitation efficiency $T_{eff}$ becomes minimum when n=(N+1)/2, i.e. at the capillary centered in the array of a plurality of capillaries, and the excitation efficiencies at other capillaries are symmetrical with the central position of the array. The minimum of the excitation efficiency $T_{effmin}$ is Equation 15:

$$T_{effmin} = T_{ram}\uparrow((N-1)/2) \quad \text{(Equation 15)}$$

Equation 15 is obviously larger than the excitation efficiency in the Nth capillary in the case of Example 6, that is the case where the laser beam is not split. With these simulation conditions, N=10 and $T_{ram}=0.929$, therefore the excitation efficiency becomes minimum in the fifth capillary, which is 69.2%. On the other hand, in Example 6, the excitation efficiency became minimum in the tenth capillary, which was 51.5%. It was revealed, therefore, that simultaneous detection of a plurality of capillaries can be performed by this technique with more efficiency. Attending this, the maximum number of capillaries which allow simultaneous detection limiting the decrease of excitation efficiency to 20% increased from 22 to 43 ($0.929^{21} \approx 0.21$). It is natural that the application of the technique shown in this example to a cylindrical capillary or an elliptic tubular capillary provides similar effects.

By application of the construction of FIG. 19 to each example of the present invention, the non-uniformity in the intensity of the laser light irradiating each capillary can be improved to make laser light with uniform intensity irradiate each capillary.

Example 10

Figure 20:
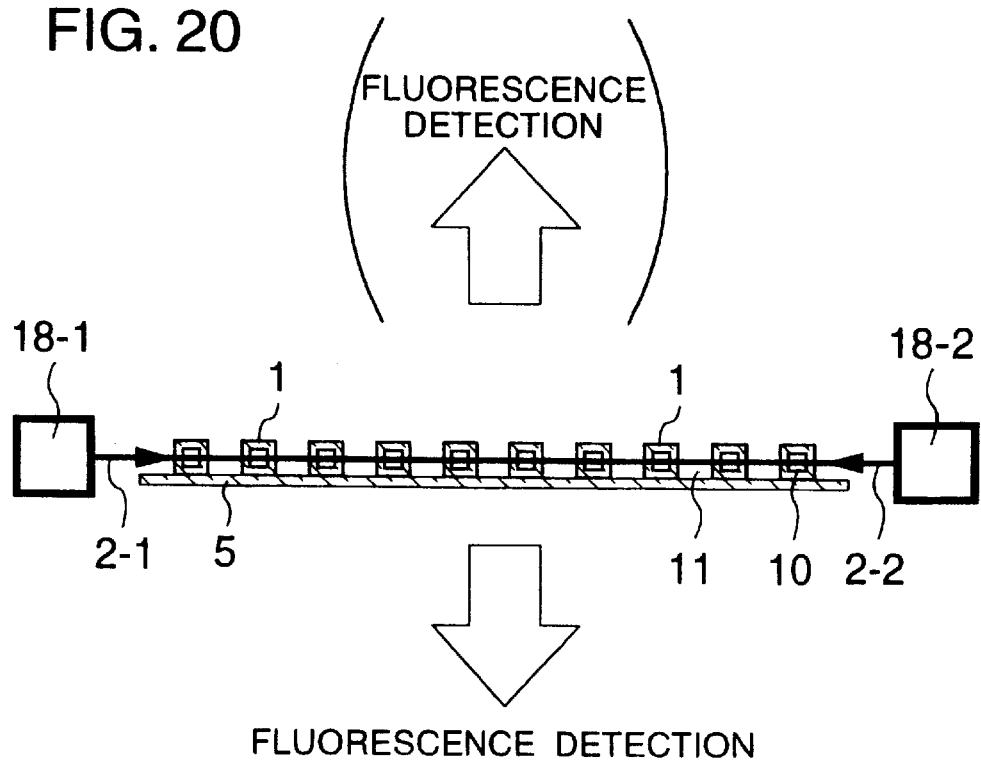
FIG. 20 is a cross-sectional view of the part where fluorescence is detected in Example 10 of the present invention.

In this example, with the experimental conditions of Example 6, as shown in FIG. 20, laser beams 2-1 and 2-2 were made to irradiate from both the two sides of the capillary array plane in which ten capillaries were aligned, using two laser sources 18-1 and 18-2. Both of the laser beams 2-1 and 2-2 were focused to 0.1 mm of a beam diameter with lenses (not shown), and were adjusted to be coaxial with each other. The other simulation conditions were made the same as those in Example 6. When N capillaries are aligned, the excitation efficiency $T_{eff}$ in the nth ($n \leq N$) capillary from one side is represented by Equation 16 if the mean transmittance of the laser beam per capillary is $T_{ram}$:

$$T_{eff} = T_{ram}\uparrow(N-1) + T_{ram}\uparrow(N-n) \quad \text{(Equation 16)}$$

The sample components migrating in a plurality of capillaries can be excited with an excitation efficiency twice as high as the excitation efficiency shown by Equation 14 obtained in the case of Example 9. The first and second terms of Equation 16 represent the excitations by the laser beams from the two laser sources, respectively. Equation 16 is normalized by the excitation efficiency at the first capillary in the case of Example 6, and $T_{eff} > 1$ means that the excitation efficiency is more than the excitation efficiency indicated by Equation 14. According to Equation 16, the excitation efficiency $T_{eff}$ becomes minimum when n=(N+1)/2, i.e. at the capillary centered in the array of a plurality of capillaries, and the excitation efficiencies at other capillaries are symmetrical with the central position of the array. The minimum of the excitation efficiency $T_{effmin}$ is Equation 17:

$$T_{effmin} = 2 \times T_{ram}\uparrow((N-1)/2) \quad \text{(Equation 17)}$$

This is obviously larger than the case of Example 6, that is the minimum $T_{ram}\uparrow(N-1)$ ($T_{ram} \leq 1$) in the case where only one laser source was used. With these simulation conditions, N=10 and $T_{ram}=0.929$, therefore the excitation efficiency becomes minimum in the fifth capillary, which is 138.4%. On the other hand, in Example 6, the excitation efficiency became minimum in the tenth capillary, which was 51.5%. It was revealed, therefore, that simultaneous detection of a plurality of capillaries can be performed by this technique with more efficiency. Attending this, the maximum number of capillaries which allow simultaneous detection limiting the decrease of excitation efficiency to 20% increased from 22 to 63 ($2 \times 0.929^{31} \approx 0.20$). It is natural that the application of the technique shown in this example to a cylindrical capillary or an elliptic tubular capillary provides similar effects.

When the construction of FIG. 20 is applied to each example of the present invention, either the wavelength of a single laser or a plurality of lasers contained by the laser beam 18-1 and the wavelength of a single laser or a plurality of lasers contained by the laser beam 18-2 arranged to be the same or different is suitable.

Example 11

Figure 21:
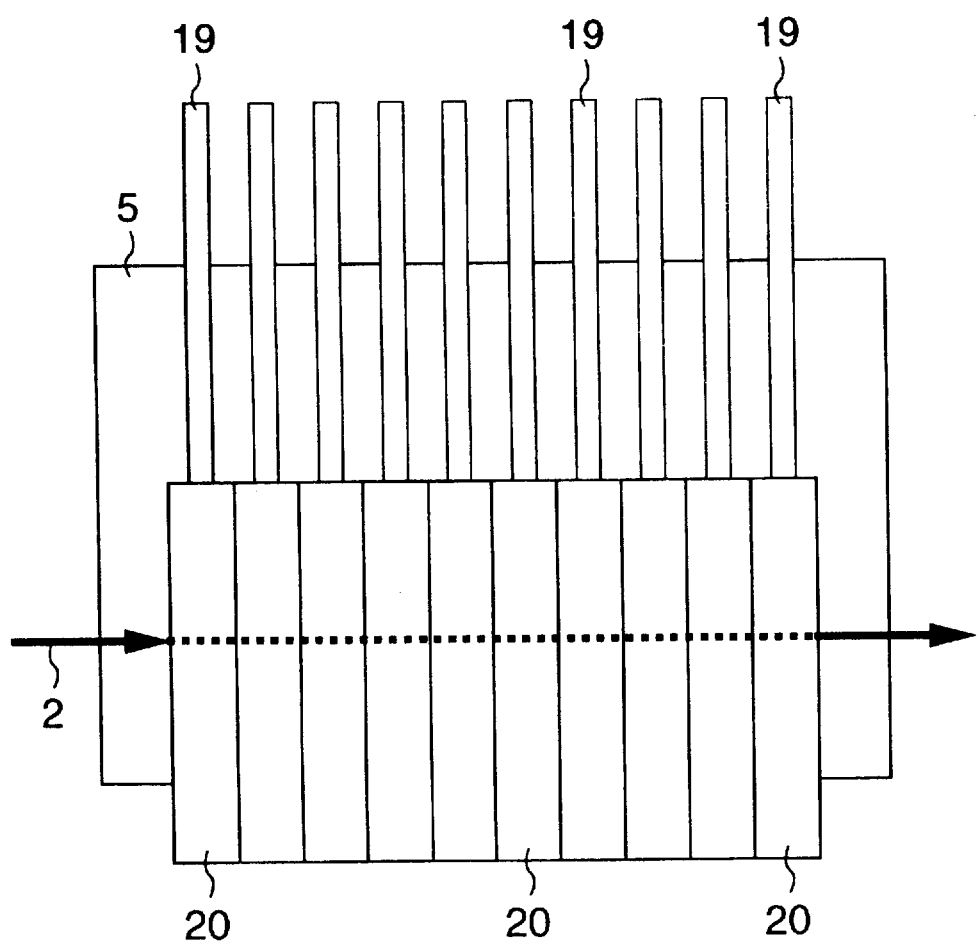
FIG. 21 is a cross-sectional view of the part where fluorescence is detected in Example 11 of the present invention.

In this example, as shown in FIG. 21, capillaries with two different shapes are connected to form one electrophoretic path, a plurality of the paths are arranged on a plane, and the fluorescence from each capillary is detected at the same time. For each eletrophoretic separation part of ten capillaries, a separation capillary 19 of a cylindrical capillary having a circular cross section with an outside diameter of 0.2 mm (R=0.1 mm) and an inside diameter of 0.1 mm (r=0.05 mm) was used, and for the capillary at the fluorescence detection site, a detection capillary 20 of a square tubular capillary having a square cross section with an outside perimeter of a square with a 0.4 mm edge and an inside perimeter of a square with a 0.1 mm edge was used. The separation capillary and the detection capillary constituting each electrophoretic path were connected with each other and aligned with a 0.4 mm pitch on a glass plate. The central axes of ten sets at a connected separation capillary and a detection capillary were made to agree. The material of both capillaries is quartz ($n_2$=1.46), whose connection surface was preliminarily made flat by polishing. Acrylamide of 4% T (total monomer concentration) and 5% C (crosslinking material concentration) containing 7M urea was injected, then it was allowed to gel. The connection part of the capillaries was immersed into a buffer solution (not shown) to avoid electric disconnection, and was set so that the sample components migrating through the separation capillary continuously migrated in the facing detection capillary. The length of the separation capillary was set to be 25 cm, and that of the detection capillary was set to be 15 cm. A window to detect fluorescence had been preliminarily formed by removing the polyimide coating from 10 mm along and all around each capillary at a position 5 cm from the position where the separation capillary was connected, and a laser was made to irradiate on the site. In other words, the migration distance was 25 cm+5 cm=30 cm. The simulation conditions other than these were made the same as those in Example 7. That is, the mean transmittance for a capillary was a high efficiency of 99.8%, and the excitation efficiency in the tenth capillary from the laser source was 98.2% of the first capillary ($0.998^9 \approx 0.982$). It was revealed that simultaneous detection of up to 804 capillaries is possible ($0.998^{803} \approx 0.20$) with the simulation conditions, assuming that the decrease of the excitation efficiency that allows simultaneous detection is limited to 20% based on the relation between the sensitivity of the detector and the dynamic range.

In general, a capillary is more expensive as its outside diameter becomes larger and inside diameter becomes smaller, i.e. as it becomes thicker, roughly in proportion to the volume of the glass. Moreover, an elliptic tubular capillary or a square tubular capillary is more expensive than a cylindrical capillary. In other words, they are advantageous for simultaneous defection of a lot of capillaries but they are expensive. However, as shown in this example, the use of the expensive capillary for a detection capillary and the inexpensive capillary for a separation capillary allows reduction of the running cost. Also, the separation capillary is removable from the detection capillary, and therefore the exchange of only the separation capillary after one analysis to perform the next analysis further reduces the cost. This is another effect of this example. Of course, a combination of capillaries with other shapes can provide similar effects. For example, as a capillary for the detecting part, a capillary having an outside diameter of 0.5 mm (outside semi-diameter: R=0.25 mm) and an inside diameter of 0.1 mm (inside semi-diameter: r=0.05 mm) may be used.

Example 12

So as to make a laser irradiate a plurality of capillaries at the same time with more efficiency, conditions for focusing a laser were investigated, and an example of a detection under optimal conditions is described below. The capillary has a cylindrical shape, therefore each capillary itself has an action of a lens, and the irradiating beam is greatly refracted when it transmits the first capillary. Since the refraction occurs in all of the capillaries, the intensity of the laser light that reaches and irradiates each capillary undesirably decreases almost exponentially according to the number of capillaries used. If $\Delta\theta$ given by Equation 9 is sufficiently small, with less damping of the intensity of the laser light, the constructions shown in FIGS. 1, 2 and 3 allow the laser to irradiate a plurality of capillaries with good efficiency at the same time and the sample components migrating in each capillary can be excited substantially at the same time.

Usually, laser irradiation to a capillary is performed with the laser focused to a size of about the inside diameter of the capillary. In a common case, laser intensity is a Gaussian distribution whose symmetry axis is the central axis of the laser beam. In other words, when the central axis of the laser beam goes into an array axis of a plurality of capillaries, the laser intensity nearly equals to an intensity giving a half width of the Gaussian distribution stated above at a position with a distance approximately half the inside semidiameter of the capillary from the array axis. Then, for simplicity, paying attention only to the laser beam that came into a position at a distance of ½ of the inside semidiameter of the capillary from the array axis 4 of the capillary (i.e. x=r/2), Equation 9 becomes:

$$\Delta\theta = (360/\pi)[-\sin^{-1}\{r/(2R)\} + \qquad \text{(Equation 18)}$$

$$\sin^{-1}\{rn_1/(2Rn_2)\} - \sin^{-1}\{n_1/(2n_2)\} + \sin^{-1}\{n_1/(2n_3)\}]$$

Considering the degree to which the laser beam spreads in a space, the shift of the laser beam at a position of the Nth capillary from the first capillary in which the laser initially enters is approximately given by $2(N-1)R\Delta\theta$. Assuming that it is the condition for simultaneous excitation of samples migrating in N capillaries (simultaneous excitation condition) that the laser intensity at the Nth capillary is equal to, or more than 1/10 of the laser intensity at the first capillary, the shift above shall be equal to or less than $\{\sqrt{10}-1\}$ times as large as r/2. In other words, Equation 19 works out:

$$2(N-1)R\Delta\theta \leq \{\sqrt{10}-1\}r/2 \qquad \text{(Equation 19)}$$

Equation 19 is the above-mentioned simultaneous excitation condition for N capillaries, wherein the number of capillaries to simultaneously excite is five or more (N≧5). Considering that the ratio R/r of the outside to inside diameters of a capillary is generally R/r≧2, the Equation 19 becomes $\Delta\theta \geq 4°$, and the above-mentioned simultaneous excitation condition becomes Equation 20 from Equation 18:

$$(360/\pi[-\sin^{-1}\{r/(2R)\}+\sin^{-1}\{rn_1/(2Rn_2)\}-\sin^{-1}\{n_1/(2n_2)\}+\sin^{-1}\{n_1/(2n_3)\}]<4° \qquad \text{(Equation 20)}$$

Assuming that it is the simultaneous excitation condition for the N capillaries described above that the laser intensity at the Nth capillary is equal to, or more than ½ of the laser intensity at the first capillary, this condition becomes Equation 21 similar to Equation 19:

$$2(N-1)R\Delta\theta \leq \{\sqrt{2} - 1\}r/2 \quad \text{(Equation 21)}$$

Considering that $N \geq 5$ and $R/r \geq 2$, the equation becomes $\Delta\theta \leq 1°$, and together with Equation 18, the simultaneous excitation condition above becomes Equation 22:

$$(360/\pi)[-\sin^{-1}\{r/(2R)\}+\sin^{-1}\{rn_1/(2Rn_2)\}-\sin^{-1}\{n_1/(2n_2)\}+\sin^{-1}\{n_1/(2Rn_3)\}] \leq 1° \quad \text{(Equation 22)}$$

Example 13

As described in Example 3, when a lot of cylindrical capillaries were aligned to detect at a time, it was more advantageous to arrange the capillaries in air than in water. The reason is that the angle of refraction indicated by Equation 9 or Equation 18 is smaller in the case of air arrangement and the condition for focusing the laser beam works out more easily. Example 3 is an ordinary case, i.e. a case where quartz ($n_2=1.46$) was used for the material of the capillary and polyacrylamide gel ($n_3=1.36$) was used for the separation medium. Therefore, by changing the conditions, the arrangement of the capillaries in water or other liquids allows more efficient simultaneous detection of a lot of capillaries. The most effective change of the conditions is to raise the refractive index of the separation medium. A method for raising the refractive index of acrylamide gel is, for example, mixing formamide (refractive index: 1.45) with a suitable concentration. Formamide is a denaturant, similar to urea, and mixing 10% of it provides an effect of increasing the resolution of electrophoresis, but mixing 20% or more of it has a defect of causing undesirable reduction of the migration speed (Electrophoresis, Vol.13, pp.484–486 (1992)). Mixing around 10% of formamide is sufficient for raising the refractive index of acrylamide gel from 1.36 to 1.40.

When a fused silica capillary ($n_2=1.46$) having an outside diameter of 0.2 mm ($R=0.1$ mm) and an inside diameter of 0.1 mm ($r=0.05$ mm) is filled with acrylamide gel whose refractive index is raised by such a method ($n_3=1.40$) and a lot of the fused silica capillaries are arranged in water ($n_1=1.33$) as shown in FIG. 12, $\Delta\leftarrow=-0.100$ from Equation 18, and a lot of capillaries come to be simultaneously irradiated with efficiency because each capillary acts as a convex lens.

Example 14

Although acrylamide gel was used in all of Examples 1 to 13 above, other separation media may be used. Using an exchangeable separation medium, a capillary itself may be reused. However, according to the refractive indexes of respective separation media, e.g. optimization of the refractive indexes of respective media and the diameter dimensions of capillaries based on Equation 9 is important for highly-sensitive and efficient simultaneous detection of the fluorescence radiating from the sample components migrating in a plurality of capillaries. Also from Equation 9, $\Delta\theta$ is not determined independently by 2R (the outside diameter of the capillary) or by 2r (the inside diameter of the capillary), but $\Delta\theta$ is determined by R/r, the ratio of the outside diameter to the inside diameter. Therefore, in each example shown above, approximately the same effect can be obtained if the ratio of the outside diameter to the inside diameter (R/r) is equal, even in a case where capillaries with different outside diameters 2R and inside diameters 2r are used.

Although acrylamide gel was used as an electrophoresis separation medium in all the examples above, a solution containing a polymer may be used as the other separation medium. Such polymers include polymers of acrylamide and its derivatives, and polymers of polysaccharides such as cellulose and its derivatives, etc. An exchangeable state of the polymer in a capillary allows repetitive use of the main body of the capillary, therefore costs or labor can be reduced.

Moreover, although fused silica was used for the material of the capillary in all of the examples above, other materials may be used. Especially, glass is a material providing various refractive indexes, and the lens action of a capillary can be controlled as is the case with the shape of a capillary. In short, more effective simultaneous detection of a lot of capillaries is possible. Only cylindrical, elliptical and square tube capillaries have been described, but other shapes may be used. Furthermore, the present invention is not limited to the examples above, and the characteristic matters described in the examples above may be combined.

A capillary gel electrophoresis allows a high-speed analysis because a higher voltage can be applied than a slab gel electrophoresis. This multiple focusing capillary array electrophoresis in which a plurality of capillaries are aligned and detected at a time is a high-throughput analytical method which provides a high-speed analysis of a lot of samples. A capillary array electrophoresis can perform introduction of samples into capillaries by electric field injection, therefore it is much easier than a slab gel electrophoresis. Moreover, on-column detection which detects fluorescence by performing a direct laser irradiation of capillaries is a high resolution technique and a highly sensitive fluorescence detection technique because it has few factors to reduce resolution of electrophoresis and a good excitation efficiency.

We claim:

1. A capillary array electrophoresis system, comprising:
    a plurality of capillaries filled with a migration medium, wherein said plurality of capillaries have transparent parts surrounded by a transparent gas and are aligned in a plane, and wherein the cross-sectional shape of each of said capillaries at the transparent part thereof is a circle;
    a light source emitting a laser beam that irradiates the transparent parts of said plurality of capillaries along the direction of alignment of said plurality of capillaries, to excite fluorophore labels of samples migrating in said plurality of capillaries; and
    a light detector that detects fluorescence radiated from said fluorophore labels from a direction crossing the direction of the alignment of said plurality of capillaries;
    wherein the cross-sectional shape of the sample injection end of each of said plurality of capillaries is different from the cross-sectional shape of the transparent part of each of said plurality of capillaries.

2. A capillary array electrophoresis system, comprising:
    a plurality of capillaries filled with a migration medium, wherein said plurality of capillaries have transparent parts surrounded by a transparent gas and are aligned in a plane, and wherein the cross-sectional shape of each of said capillaries at the transparent part thereof is a circle;
    a light source emitting a laser beam that irradiates the transparent parts of said plurality of capillaries along the direction of alignment of said plurality of capillaries, to excite fluorophore labels of samples migrating in said plurality of capillaries; and
    a light detector that detects fluorescence radiated from said fluorophore labels from a direction crossing the direction of the alignment of said plurality of capillaries;

wherein the cross-sectional area of the sample injection end of each of said plurality of capillaries is different from the cross-sectional area of the transparent part of each of said plurality of capillaries.

3. A capillary array electrophoresis system, comprising:
a plurality of capillaries filled with a migration medium, wherein said plurality of capillaries have transparent parts surrounded by a transparent gas and are aligned in a plane, wherein the cross-sectional shape of each of said capillaries at the transparent part thereof is a circle, and wherein an antireflection coating layer is formed on the surface of the transparent part of each of said plurality of capillaries;
a light source emitting a laser beam that irradiates the transparent parts of said plurality of capillaries along the direction of alignment of said plurality of capillaries, to excite fluorophore labels of samples migrating in said plurality of capillaries; and
a light detector that detects fluorescence radiated from said fluorophore labels from a direction crossing the direction of the alignment of said plurality of capillaries.

4. A capillary array electrophoresis system, comprising:
a plurality of capillaries filled with a migration medium, wherein said plurality of capillaries have transparent parts surrounded by a transparent gas and are aligned in a plane, and wherein the cross-sectional shape of each of said capillaries at the transparent part thereof is a circle;
a light source emitting laser light;
a beam splitter that divides said laser light into two laser beams, wherein said two laser beams irradiate the transparent parts of said plurality of capillaries from two different directions along the direction of alignment of said plurality of capillaries, and said two laser beams excite fluorophore labels of samples migrating in said plurality of capillaries; and
a light detector that detects fluorescence radiated from said fluorophore labels from a direction crossing the direction of the alignment of said plurality of capillaries.

5. A capillary array electrophoresis system, comprising:
a plurality of capillaries filled with a migration medium, wherein said plurality of capillaries have transparent parts surrounded by a transparent gas and are aligned in a plane, and wherein the cross-sectional shape of each of said capillaries at the transparent part thereof is a circle,
two light sources each emitting a laser beam, wherein the laser beams from said two light sources irradiate the transparent parts of said plurality of capillaries from two different directions along the direction of alignment of said plurality of capillaries, and wherein said laser beams excite fluorophore labels of samples migrating in said plurality of capillaries; and
a light detector that detects fluorescence radiated from said fluorophore labels from a direction crossing the direction of the alignment of said plurality of capillaries.

6. A capillary array electrophoresis system, comprising:
a plurality of capillaries filled with a migration medium, wherein said plurality of capillaries have transparent parts surrounded by a transparent gas and are aligned in a plane, and wherein the cross-sectional shape of each of said capillaries at the transparent part thereof is a circle;
a light source emitting a laser beam that irradiates the transparent parts of said plurality of capillaries along the direction of alignment of said plurality of capillaries, to excite fluorophore labels of samples migrating in said plurality of capillaries; and
a light detector that detects fluorescence radiated from said fluorophore labels from a direction crossing the direction of the alignment of said plurality of capillaries;
wherein the cross-sectional shape of the sample injection end of each of said plurality of capillaries is different from the cross-sectional shape of the transparent part of each of said plurality of capillaries; and
wherein the following relation is satisfied:

$$(360°/\pi)[-\sin^{-1}\{r/(2R)\}+\sin^{-1}\{rn_1/(2Rn_2)\}-\sin^{-1}\{n_1/(2n_2)\}+\sin^{-1}\{n_1/(2n_3)\}] \leq 4°;$$

where R is an outer radius of each of said plurality of capillaries, r is an inner radius of each of said plurality of capillaries, $n_1$ is a refractive index of a medium in the outside of the transparent parts of said plurality of capillaries, $n_2$ is a refractive index of the transparent parts of said plurality of capillaries, and $n_3$ is a refractive index of said migration medium.

7. A capillary array electrophoresis system, comprising:
a plurality of capillaries filled with a migration medium, wherein said plurality of capillaries have transparent parts surrounded by a transparent gas and are aligned in a plane, and wherein the cross-sectional shape of each of said capillaries at the transparent part thereof is a circle;
a light source emitting a laser beam that irradiates the transparent parts of said plurality of capillaries along the direction of alignment of said plurality of capillaries, to excite fluorophore labels of samples migrating in said plurality of capillaries; and
a light detector that detects fluorescence radiated from said fluorophore labels from a direction crossing the direction of the alignment of said plurality of capillaries;
wherein the cross-sectional area of the sample injection end of each of said plurality of capillaries is different from the cross-sectional area of the transparent part of each of said plurality of capillaries; and
wherein the following relation is satisfied:

$$(360°/\pi)[-\sin^{-1}\{r/(2R)\}+\sin^{-1}\{rn_1/(2Rn_2)\}-\sin^{-1}\{n_1/(2n_2)\}+\sin^{-1}\{n_1/(2n_3)\}] \leq 4°;$$

where R is an outer radius of each of said plurality of capillaries, r is an inner radius of each of said plurality of capillaries, $n_1$ is a refractive index of a medium in the outside of the transparent parts of said plurality of capillaries, $n_2$ is a refractive index of the transparent parts of said plurality of capillaries, and $n_3$ is a refractive index of said migration medium.

8. A capillary array electrophoresis system, comprising:
a plurality of capillaries filled with a migration medium, wherein said plurality of capillaries have transparent parts surrounded by a transparent gas and are aligned in a plane, wherein the cross-sectional shape of each of said capillaries at the transparent part thereof is a circle, and wherein an antireflection coating layer is formed on the surface of the transparent part of each of said plurality of capillaries;

a light source emitting a laser beam that irradiates the transparent parts of said plurality of capillaries along the direction of alignment of said plurality of capillaries, to excite fluorophore labels of samples migrating in said plurality of capillaries; and a light detector that detects fluorescence radiated from said fluorophore labels from a direction crossing the direction of the alignment of said plurality of capillaries;

wherein the following relation is satisfied:

$$(360°/\pi)[-\sin^{-1}\{r/(2R)\}+\sin^{-1}\{rn_1/(2Rn_2)\}-\sin^{-1}\{n_1/(2n_2)\}+\sin^{-1}\{n_1/(2n_3)\}]\leq 4°;$$

where R is an outer radius of each of said plurality of capillaries, r is an inner radius of each of said plurality of capillaries, $n_1$ is a refractive index of a medium in the outside of the transparent parts of said plurality of capillaries, $n_2$ is a refractive index of the transparent parts of said plurality of capillaries, and $n_3$ is a refractive index of said migration medium.

9. A capillary array electrophoresis system, comprising:

a plurality of capillaries filled with a migration medium, wherein said plurality of capillaries have transparent parts surrounded by a transparent gas and are aligned in a plane, and wherein the cross-sectional shape of each of said capillaries at the transparent part thereof is a circle;

a light source emitting laser light;

a beam splitter that divides said laser light into two laser beams, wherein said two laser beams irradiate the transparent parts of said plurality of capillaries from two different directions along the direction of alignment of said plurality of capillaries, and said two laser beams excite fluorophore labels of samples migrating in said plurality of capillaries; and a light detector that detects fluorescence radiated from said fluorophore labels from a direction crossing the direction of the alignment of said plurality of capillaries;

wherein the following relation is satisfied:

$$(360°/\pi)[-\sin^{-1}\{r/(2R)\}+\sin^{-1}\{Rn_1/(2Rn_2)\}-\sin^{-1}\{n_1/(2n_2)\}+\sin^{-1}\{n_1/(2n_3)\}]\leq 4°;$$

where R is an outer radius of each of said plurality of capillaries, r is an inner radius of each of said plurality of capillaries, $n_1$ is a refractive index of a medium in the outside of the transparent parts of said plurality of capillaries, $n_2$ is a refractive index of the transparent parts of said plurality of capillaries, and $n_3$ is a refractive index of said migration medium.

10. A capillary array electrophoresis system, comprising:

a plurality of capillaries filled with a migration medium, wherein said plurality of capillaries have transparent parts surrounded by a transparent gas and are aligned in a plane, and wherein the cross-sectional shape of each of said capillaries at the transparent part thereof is a circle;

two light sources each emitting a laser beam, wherein the laser beams from said two light sources irradiate the transparent parts of said plurality of capillaries from two different directions along the direction of alignment of said plurality of capillaries, and said laser beam excite fluorophore labels of samples migrating in said plurality of capillaries; and a light detector that detects fluorescence radiated from said fluorophore labels from a direction crossing the direction of the alignment of said plurality of capillaries;

wherein the following relation is satisfied:

$$(360°/\pi)[-\sin^{-1}\{r/(2R)\}+\sin^{-1}\{rn_1/(2Rn_2)\}-\sin^{-1}\{n^1/(2n_2)\}+\sin^{31\ 1}\{n_1/(2n_3)\}]\leq 4°;$$

where R is an outer radius of each of said plurality of capillaries, r is an inner radius of each of said plurality of capillaries, $n_1$ is a refractive index of a medium in the outside of the transparent parts of said plurality of capillaries, $n_2$ is a refractive index of the transparent parts of said plurality of capillaries, and $n_3$ is a refractive index of said migration medium.

11. A capillary array electrophoresis system, comprising:

a plurality of capillaries filled with a migration medium, wherein said plurality of capillaries have transparent parts surrounded by a transparent gas and are aligned in a plane, and wherein the cross-sectional shape of each of said capillaries at the transparent part thereof is a circle;

a light source emitting a laser beam that irradiates the transparent parts of said plurality of capillaries along the direction of alignment of said plurality of capillaries, to excite fluorophore labels of samples migrating in said plurality of capillaries; and a light detector that detects fluorescence radiated from said fluorophore labels from a direction crossing the direction of the alignment of said plurality of capillaries;

wherein the following relation is satisfied:

$$(360/\pi)[-\sin^{-1}\{r/(2R)\}+\sin^{-1}\{rn_1/(2Rn_2)\}-\sin^{-1}\{n_1/(2n_2)\}+\sin^{-1}\{n_1/(2n_3)\}]\leq 0°;$$

where R is an outer radius of each of said plurality of capillaries, r is an inner radius of each of said plurality of capillaries, $n_1$ is a refractive index of a medium in the outside of the transparent parts of said plurality of capillaries, $n_2$ is a refractive index of the transparent parts of said plurality of capillaries, and $n_3$ is a refractive index of said migration medium.

* * * * *